(12) United States Patent
Goldsmith et al.

(10) Patent No.: US 11,710,547 B2
(45) Date of Patent: Jul. 25, 2023

(54) METHODS AND SYSTEMS FOR PROVIDING PERSONALISED MEDICINE TO A PATIENT

(71) Applicant: Closed Loop Medicine Ltd., Cambridge (GB)

(72) Inventors: Paul Goldsmith, London (GB); Hakim Adam Yadi, London (GB); Andrew John McGlashan Richards, Cambridge (GB); Felicity Kate Sartain, London (GB); David Cox, London (GB); David O'Regan, London (GB)

(73) Assignee: CLOSED LOOP MEDICINE LTD., Cambridge (GB)

( * ) Notice: Subject to any disclaimer, the term of this patent is extended or adjusted under 35 U.S.C. 154(b) by 268 days.

(21) Appl. No.: 16/860,665

(22) Filed: Apr. 28, 2020

(65) Prior Publication Data
US 2020/0350073 A1    Nov. 5, 2020

Related U.S. Application Data

(60) Provisional application No. 62/841,967, filed on May 2, 2019.

(51) Int. Cl.
*G16H 20/10* (2018.01)
*G16H 10/60* (2018.01)
(Continued)

(52) U.S. Cl.
CPC .......... *G16H 20/10* (2018.01); *A61B 5/0022* (2013.01); *A61B 5/021* (2013.01); *A61B 5/024* (2013.01);
(Continued)

(58) Field of Classification Search
CPC ...... G16H 10/00–80/00; A61B 1/00–2576/026
See application file for complete search history.

(56) References Cited

U.S. PATENT DOCUMENTS

| 5,605,911 A | * | 2/1997 | Olney | .................. | A61K 45/06 |
| | | | | | 514/315 |
| 5,629,336 A | * | 5/1997 | Hutson | .................. | A61P 43/00 |
| | | | | | 514/812 |

(Continued)

FOREIGN PATENT DOCUMENTS

| WO | WO-2005023291 A2 | * | 3/2005 | ............. A61K 38/26 |
| WO | WO-2008077092 A3 | * | 8/2008 | ......... A61K 31/4178 |

(Continued)

OTHER PUBLICATIONS

Bertsimas et al., "Personalized Diabetes Management Using Electronic Medical Records," Diabetes Care 2017;40:210-217 (Year: 2017).*

(Continued)

*Primary Examiner* — Jonathon A. Szumny
(74) *Attorney, Agent, or Firm* — Squire Patton Boggs (US) LLP

(57) ABSTRACT

The present disclosure relates to methods and systems suitable for use in identifying and providing personalised medicine to a patient. In some aspects, systems and method generate a co-therapy regimen for a patient suffering from a disease or condition. An identification of a co-therapy suitable to treat the disease or condition is received. A desired patient endpoint and a patient position are received, wherein the patient position is defined relative to the desired patient endpoint. A dataset relating to the patient is stored. The dataset comprises one or more patient data based on patient-related measurements. The dataset, the patient position and the desired patient endpoint are processed to generate a regimen for the co-therapy. The regimen is stored in a database.

23 Claims, 4 Drawing Sheets

(51) Int. Cl.
| | |
|---|---|
| G16H 20/70 | (2018.01) |
| G16H 40/67 | (2018.01) |
| G16H 50/50 | (2018.01) |
| G16H 50/20 | (2018.01) |
| A61B 5/00 | (2006.01) |
| A61B 5/021 | (2006.01) |
| A61B 5/024 | (2006.01) |
| A61B 5/145 | (2006.01) |
| A61K 31/4045 | (2006.01) |
| A61K 31/4418 | (2006.01) |
| A61K 31/485 | (2006.01) |

(52) U.S. Cl.
CPC ........ *A61B 5/14532* (2013.01); *A61B 5/4824* (2013.01); *A61B 5/4848* (2013.01); *A61B 5/7264* (2013.01); *A61K 31/4045* (2013.01); *A61K 31/4418* (2013.01); *A61K 31/485* (2013.01); *G16H 10/60* (2018.01); *G16H 20/70* (2018.01); *G16H 40/67* (2018.01); *G16H 50/20* (2018.01); *G16H 50/50* (2018.01); *A61B 2560/0252* (2013.01)

(56) References Cited

U.S. PATENT DOCUMENTS

| | | | | |
|---|---|---|---|---|
| 8,992,464 | B2* | 3/2015 | Bashan | A61B 5/4839 600/365 |
| 10,231,664 | B2* | 3/2019 | Ganesh | A61H 23/02 |
| 2003/0028031 | A1* | 2/2003 | Xitian | C07D 211/90 546/318 |
| 2005/0023291 | A1 | 2/2005 | Hynes et al. | |
| 2006/0100667 | A1* | 5/2006 | Machado | A61N 1/05 607/2 |
| 2007/0049576 | A1* | 3/2007 | Barlow | A61P 25/20 514/297 |
| 2007/0150026 | A1* | 6/2007 | Bourget | A61N 1/37252 607/46 |
| 2007/0292883 | A1* | 12/2007 | Ossovskaya | A61P 11/00 514/415 |
| 2008/0275309 | A1* | 11/2008 | Stivoric | G16H 10/60 600/300 |
| 2008/0288023 | A1* | 11/2008 | John | G16H 20/40 607/59 |
| 2010/0073170 | A1* | 3/2010 | Siejko | A61B 5/0205 706/11 |
| 2010/0235195 | A1* | 9/2010 | Firminger | G16H 40/67 705/26.1 |
| 2012/0108984 | A1 | 5/2012 | Bennett et al. | |
| 2012/0116194 | A1* | 5/2012 | Gross | A61B 5/00 600/323 |
| 2014/0310025 | A1* | 10/2014 | Sayada | G16B 50/00 705/2 |
| 2014/0323536 | A1* | 10/2014 | Sabovic | A61P 9/10 514/381 |
| 2015/0133886 | A1* | 5/2015 | Morris | A61M 5/172 604/67 |
| 2016/0175310 | A1* | 6/2016 | Garcia Castellano | A61P 21/00 514/249 |
| 2016/0224760 | A1* | 8/2016 | Peták | G16H 50/70 |
| 2016/0350509 | A1* | 12/2016 | Sharma | A61B 5/02055 |
| 2018/0140835 | A1* | 5/2018 | Sharma | G16H 10/60 |
| 2019/0367903 | A1* | 12/2019 | Domenyuk | C40B 40/08 |
| 2020/0321096 | A1* | 10/2020 | Mould | G16H 50/20 |
| 2021/0106592 | A1* | 4/2021 | Mehra | A61K 31/55 |
| 2021/0259993 | A1* | 8/2021 | Witkin | A61P 25/24 |

FOREIGN PATENT DOCUMENTS

| | | | | |
|---|---|---|---|---|
| WO | WO-2012089318 | A1* | 7/2012 | ........ G06F 19/3456 |
| WO | WO 2017/220734 | | 12/2017 | |
| WO | WO-2017214630 | A1* | 12/2017 | .......... A61B 5/0002 |
| WO | 2018020239 | | 2/2018 | |
| WO | 2018049250 | | 3/2018 | |
| WO | 2019008571 | | 1/2019 | |

OTHER PUBLICATIONS

Baron et al., "Next Steps for Patients Who Fail to Respond to Cognitive Behavioral Therapy for Insomnia (CBT-I): the Perspective from Behavioral Sleep Medicine Psychologists," Curr Sleep Medicine Rep (2017) 3:327-332 (Year: 2017).*

Liang et al., "Estimating individualized optimal combination therapies through outcome weighted deep learning algorithms," Statistics in Medicine. 2018;37:3869-3886. (Year: 2018).*

Linden et al., "Clinical Effectiveness of Non-Drug Treatment for Hypertension: a Meta-Analysis," Annals of Behavioral Medicine, vol. 16, Issue 1, 1994, pp. 35-45, https://doi.org/10.1093/abm/16.1.35 (Year: 1994).*

WIPO, International Search Report and Written Opinion dated Aug. 20, 2020, in PCT/GB2020/051027, 20 pgs.

* cited by examiner

METHODS AND SYSTEMS FOR PROVIDING PERSONALISED MEDICINE TO A PATIENT

CROSS-REFERENCE TO RELATED APPLICATIONS

This application claims priority to U.S. Provisional Application No. 62/841,967, entitled "Methods and Systems for Providing Personalised Medicine to a Patient," filed May 2, 2019, which is hereby incorporated by reference.

BACKGROUND

The present disclosure relates to methods and systems suitable for use in identifying and providing personalised medicine to a patient in need thereof, particularly in which a co-therapy is to be used wherein two or more two dosage regimens are provided. The methods and systems may be used to assess the efficacy of dosage forms in a patient utilising a variety of data inputs to provide the personalised medicine. It may also predict suitable dosage regimens for a particular patient.

Patients are routinely prescribed medicine by healthcare providers for the treatment of a range of diseases and conditions. The medicine is to be taken by the patient in accordance with instructions provided by a healthcare provider, which together form a dosage regimen. The dosage regimen is based upon clinical trials that are conducted on a group of patients, and in which the effect of one medicine is compared to another. Clinical trials provide dosage regimens that are generic and not personalised to the particular patient requiring treatment.

Further, patients do not typically have immediate access to healthcare providers. This means that they often have to wait weeks for a new appointment before they are able to discuss their treatment with their healthcare provider, and modify their treatment regimen.

To exacerbate this situation, combinations of therapies (co-therapy regimens) are far less studied than monotherapies, with healthcare providers often prescribing therapies comprising combinations of medicines that have not necessarily been through rigorous clinical trials. Further, NICE guidelines for medicines are usually specific to a particular condition, whereas patients usually suffer co-morbidities.

This means that patients prescribed co-therapies may experience lower levels of care than could be offered by treatment regimens tailored specifically for the individual patient. This may increase health complications and delay or prevent successful treatment of the disease or condition. It may also lead to a decrease in patient compliance as the patient does not feel that the treatment is working or is suitable for them.

In addition to the above, there are other reasons for non-adherence of patients to their medication. These include patients forgetting to take their medicines, off-putting side effects, a lack of tangible efficacy of the medication, greater than once daily frequency of administration, inability to understand complex dosing instructions, and patients exercising their prerogative of choice for a variety of personal or social reasons.

Furthermore, over time the efficacy of a particular medication, or the patient's perception of the efficacy, may decrease due to changes in the patient that are caused by factors unrelated to the medication itself. For example, changes in the lifestyle of the patient may affect their perception of efficacy of the medication, or the actual efficacy of the medication. This may discourage the patient from continuing with the course of treatment. Currently there is no way to capture the complex interdependency between the overall state of the patient and the efficacy of their medication, nor is there a way to determine or predict how a change to the state of the patient may impinge upon the actual or perceived efficacy of the medication.

In view of the above, there is a need in the art to provide methods and systems for providing personalised medicine and address one or more of the above-mentioned problems. There is also the need to provide methods and systems for monitoring and providing co-therapies for "at risk" individuals, such as those with co-morbidities, in drug rehabilitation, with psychological vulnerabilities or with compromised immune systems.

SUMMARY

The present disclosure provides a reliable and efficient means for providing personalised medicine to a patient in need thereof.

According to a first aspect of the present disclosure, there is provided a method of generating a co-therapy regimen for a patient suffering from a disease or condition, the method comprising the steps of:
  a) establishing a desired patient endpoint;
  b) identifying the patient position relative to the desired patient endpoint;
  c) generating or modifying a dataset relating to the patient, based on one or more patient-related measurements; and
  d) processing the dataset, the patient position and the desired patient endpoint to generate the co-therapy regimen.

The method of the first aspect of the present disclosure provides a personalised co-therapy regimen by accurately predicting the co-therapy regimen that is suitable to treat a disease in a particular patient based upon data related to that patient.

According to a second aspect of the present disclosure, there is provided a method of treating a patient suffering from a disease or condition, the method comprising the steps of:
  a) selecting a co-therapy suitable to treat the disease or condition;
  b) establishing a desired patient endpoint;
  c) identifying the patient position relative to the desired patient endpoint;
  d) generating or modifying a dataset relating to the patient, based on one or more patient-related measurements;
  e) processing the dataset, the patient position and the desired patient endpoint to produce a regimen for the co-therapy; and
  f) administering the co-therapy to the patient according to the regimen.

The second aspect of the present disclosure provides a personalised method of treating a patient suffering from a disease or condition. This may be in the form of an iterative process in which a co-therapy is administered to a patient, and then additional data related to the patient is processed to provide a modified co-therapy. This helps to maintain the optimal treatment of the disease or condition in the dynamic patient environment.

According to a third aspect of the present disclosure, there is provided a system for generating a co-therapy regimen for a patient suffering from a disease or condition, the system comprising at least one data processing device having at least one processor, wherein the system is configured to:
receive an identification of a co-therapy suitable to treat the disease or condition;
receive a desired patient endpoint and a patient position, wherein the patient position is defined relative to the desired patient endpoint;
store a dataset relating to the patient, the dataset comprising one or more patient data based on patient-related measurements;
process the dataset, the patient position and the desired patient endpoint to generate a regimen for the co-therapy; and
output the regimen.

The system of the third aspect of the present disclosure provides a system capable of capturing data relating to the state of the patient and analysing this data to characterise the state of the patient. Based on this characterisation, a regimen for the co-therapy can be generated and outputted by the system, where this regimen is personalised to the current state of the patient. The system can iteratively re-assess the patient state and update the co-therapy regimen where necessary. This helps to maintain the optimal treatment of the disease or condition in the dynamic patient environment.

The present disclosure can provide advantages to patients, particularly in terms of medication compliance and their actual and perceived health. It also provides benefits to healthcare providers by providing treatment regimens in cases in which a variety of factors may determine the suitability of a therapy. For examples, it is known that both CBT and exercise therapy are helpful in managing chronic pain, as are certain drugs such as neuromodulators (for instance tricyclic antidepressants), and that the timing and that duration of each is ideally coordinated with the other.

The claimed methods and system may also be of benefit to highly variable practices in clinical care, particularly in "complex" or "at risk" patients where traditionally prescribed medication may potentially result in toxicity or suboptimal therapy. The present disclosure may also alleviate problems associated with a healthcare provider relying upon previous experience to personalise a treatment therapy in complex situations that lack specific dosing recommendations.

A particular advantage of the present disclosure is its value in the dosing of non-drug therapies, such as behavioural interventions. A drug typically has a reasonably predictable translation in efficacy from its pharmacodynamic response on the day it is given in clinic, i.e. an understood effect within 3 days or 3 weeks later when taken at home. Prior to the present disclosure, the way a patient interprets and responds to a non-drug intervention, for example a behavioural therapy, may vary depending on how this treatment is delivered and by whom. For instance, it may be affected by whether it is delivered by a clinician at a clinic, at a later time point (treatment/motivational fade) or if delivered electronically from day-to-day, hour-to-hour or even minute-to-minute. It may also depend upon the mental state, location and context, history and/or time-points of other drug and non-drug therapies, inter alia, as well as the amount and time of therapy delivery.

Other features and advantages of all aspects of the present disclosure will become apparent from the following detailed description which, when taken in combination with the accompanying drawings and examples, illustrate the principle aspects of the present disclosure.

DETAILED DESCRIPTION

Figure 1:
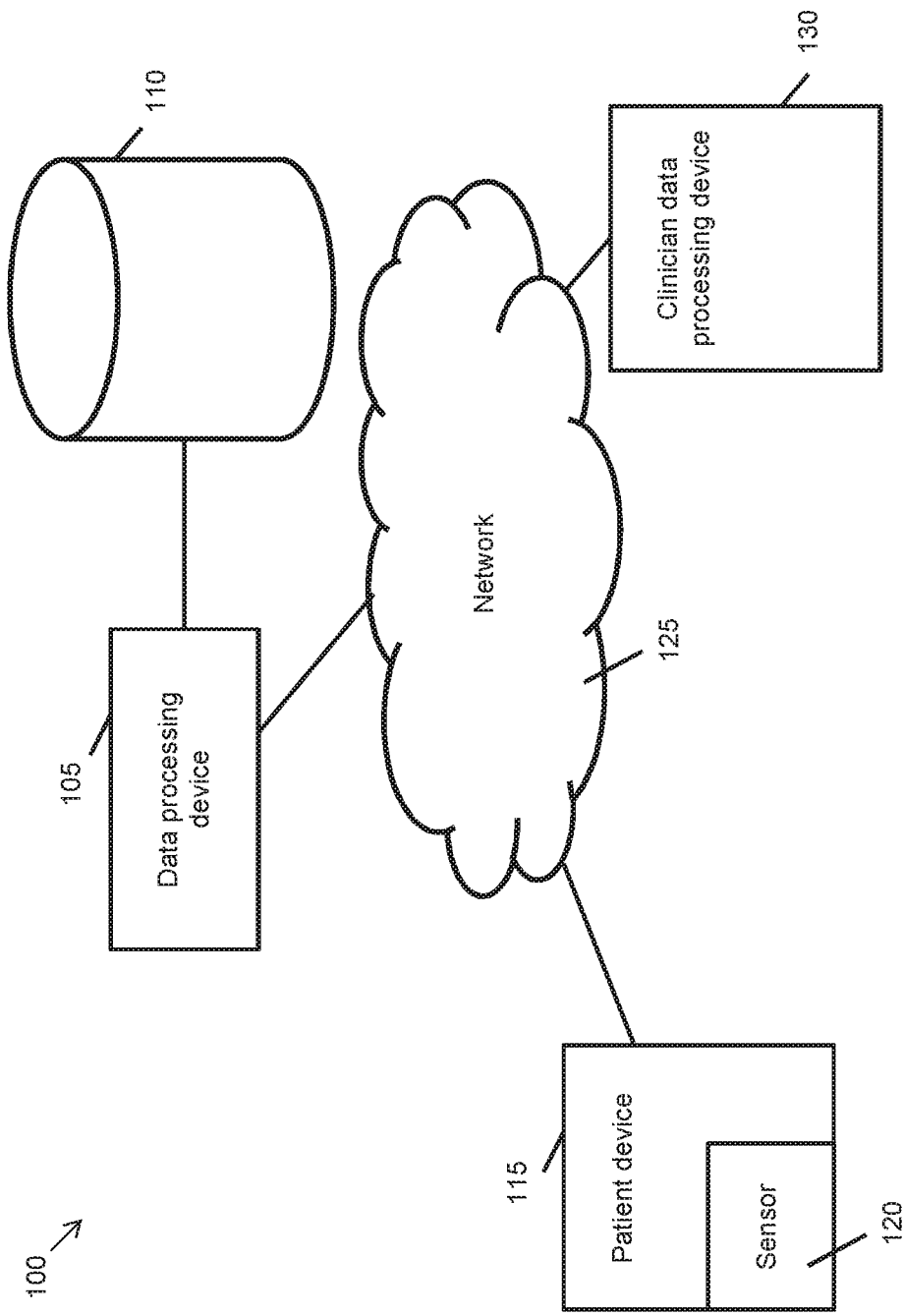
FIG. 1 shows a system suitable for implementing any of the methods described in this specification in accordance with an embodiment.

The present disclosure provides personalised medicine to a patient, in particular to treat a disease or condition from which the patient is suffering. The personalised medicine may be provided in the form of co-therapy which may include one or more pharmacological therapies and/or one or more non-pharmacological therapies.

The method of the first aspect of the present disclosure may be used to generate, or produce, a personalised medicine for a patient. The personalised medicine comprises a co-therapy regime that is suitable for use in the treatment of a disease or condition from which the patient is suffering.

As used herein, a "co-therapy regimen", "regimen for the co-therapy" or any similar term, is a course of two or more (i.e. at least two) therapies that are to be administered to the patient with the intention of treating a disease or condition. The method may comprise two, three, four, five, six, seven or more different therapies. The regimen may comprise an associated amount, intensity and/or frequency (which may be relative to the administration of a previous dosage or to the time of day) for each of the therapies individually. Preferably the co-therapy comprises different therapies. This means that it is preferable that the therapies are not the same type of therapy, for instance, they are not two types of drugs both acting on the opiate pathway aimed at treating the same disease or condition. It is particularly preferred that the therapies do not have the same mode of action on the patient. For instance, in this particular case, while a co-therapy may provide inflammatory relief, the co-therapy may not comprise two NSAID therapies. In a particular embodiment, the co-therapies are not all hormone-based therapies.

Said therapies may be administered sequentially or concomitantly and by any route, with administration intervals between the same and/or different therapies forming part of the co-therapy regimen. For example, the co-therapy regimen may require two therapies to be administered to the patient sequentially each day or every other day. Alternatively, one or more of the therapies may be administered as required by the patient (i.e. "on demand"), or at a time at which data relating to the patient indicates that a therapy should be administered. The skilled person will know and understand the range of therapies that may be administered to a patient suffering from a particular disease or condition.

The term "one or more" means that there must be at least one of whatever follows said term, such as one, two, three, four, five six, seven, eight, nine, ten, or more.

A "therapy" may be based upon a pharmacological therapy, such as a pharmaceutical drug therapy, or a non-pharmacological therapy, such as cognitive behavioural therapy (CBT), light therapy, exercise therapy, hypnosis, massage, reflexology, and meditation. As such, the term "therapy" is to be interpreted broadly and includes any course of action that is, or may be, suitable for use in the treatment of a disease or condition.

The term "cognitive behavioural therapy" is any therapy which influences or alters the way a patient thinks and/or behaves. Its prototypical form is as a 'talking therapy' for mental health problems such as anxiety and depression, but it is understood in the art that similar approaches of altering the way a patient thinks and behaves is applicable to multiple other conditions, such as chronic pain, functional disorders, COPD and diabetes, such as how a patient interprets symptoms, how they interpret their interaction with the world and the future, how they control their attention; then how they behave, such as sleep/wake cycles, exercise patterns and diet. CBT may also help patients deal with overwhelming problems in a more positive way by breaking them down into smaller parts. CBT is based, in part, on the concept that a patient's thoughts, feelings, physical sensations and actions are interconnected, and that negative thoughts and feelings can cause or exacerbate certain diseases and conditions. CBT has been well documented in the treatment of depression, anxiety, obsessive compulsive disorder, panic disorder, post-traumatic stress disorder, phobias, eating disorders, such as anorexia and bulimia, sleep problems such as insomnia (in which case it may be referred to as cognitive behavioural therapy for insomnia (CBTi)), and problems associated with drug and alcohol misuse. CBT may also be used for treatment of patients with long-term health conditions such as chronic pain, COPD, diabetes, headaches, irritable bowel syndrome (IBS) and fatigue states such as chronic fatigue syndrome (CFS). Whilst it is generally believed that CBT alone cannot cure physical symptoms of IBS and CFS, it may help people cope better with their symptoms.

The term "administered" is one of the art and means that a therapy is provided, or given, to the patient. In relation to the present disclosure, it may be immaterial how the therapies are administered to the patient. For instance, a therapy may be administered to a patient by a healthcare provider or another third-party. The therapy may be administered by an electronic device, such as a smartphone or other handheld device, either automatically or in direct response to user input from the patient, a healthcare provider or another third-party. Alternatively, the patient may administer the therapy himself or herself, such as by taking tablets or meditating. The electronic device may act on instructions provided by a second electronic device that is located remotely from the electronic device, such as a Cloud-based server, where such instructions are transmitted to the electronic device over a network, e.g. the internet or a cellular network.

When a therapy is a pharmacological therapy, any suitable route may be used to administer said therapy. Preferably the route of administration is by oral, rectal, nasal, topical (including buccal and sublingual), transdermal, intrathecal, transmucosal or parenteral (including subcutaneous, intramuscular, intravenous and intradermal) administration. Pharmaceutical compositions useful in a pharmacological therapy may be formulated in unit dosage form, for instance in tablets and sustained release capsules, and in liposomes. Alternatively, pharmaceutical compositions may be provided as un-dosed gels, liquids and syrups to be dosed (by the patient, third-party or an automatic dosage device) prior to administration. Dosage forms useful in relation to the present disclosure may be prepared by any methods well known in the art of pharmacy. It is envisaged and preferable that a dosage form may be provided in a "smart pack", i.e. a device that monitors the administration of a medicament to a patient. Such smart packs may be used to provide data to the patient and/or a third-party (for instance, a healthcare provider) on the patient's compliance with the co-therapy regimen. Said data may also be used in the present disclosure to modify the dataset as outlined below.

It may be the case that a patient has access only to unit dosage forms containing certain amounts of active pharmaceutical ingredients. If this is the case, the co-therapy generated in the first aspect of the present disclosure may "round" the dosage regimen in increments that are available to the patient. For instance, if the patient has access to unit dosages comprising 0.2 mg and 0.5 mg of melatonin, then the method may generate a co-therapy regimen that is limited to increments of 0.2 mg and 0.5 mg of melatonin, for instance 0.2, 0.5, 0.7, 0.9, 1.0, 1.2, 1.4, 1.5, 1.7, 1.9 and 2.0 mg of melatonin.

When a therapy is a non-pharmacological therapy, any suitable route may be used to administer said therapy. Preferably a non-pharmacological therapy is administered by an electronic device, such as a computer, a smartphone or another handheld device. The non-pharmacological therapy may be administered either automatically or in direct response to user input from the patient, a healthcare provider or another third-party. The electronic device may act on instructions provided by a second electronic device that is located remotely from the electronic device, such as a Cloud-based server, where such instructions are transmitted to the electronic device over a network, e.g. the internet or a cellular network.

The term "treatment" includes the amelioration of the disease or condition, or a symptom or symptoms thereof. Treatment also includes the amelioration of the side-effects of another therapy, such as a pharmacological therapy. Treatment also includes the reduction in a patient's dependence on another pharmacological drug, or behaviour. "Amelioration" is an improvement, or perceived improvement, in the patient's condition, or a change in a patient's condition that makes it, or side-effects, increasingly tolerable.

In relation to a patient suffering from a disease or condition, the term "suffering" includes the patient having the disease or condition. It also covers patients expecting to suffer from the disease or condition, for instance when the method is used as a preventative measure.

The term "comprises", and variations thereof, do not have a limiting meaning where these terms appear in the description and claims. Such terms will be understood to imply the inclusion of a stated step or element or group of steps or elements but not the exclusion of any other step or element or group of steps or elements.

The term "consisting of" means including, and limited to, whatever follows the phrase "consisting of". Thus, the phrase "consisting of" indicates that the listed elements are required or mandatory, and that no other elements may be present for that particular feature.

The term 'the Cloud', or equivalently 'Cloud-based', should be understood to be a reference to one or more configurable computing resources that can be called upon to perform tasks according to need. The computing resources are located remotely from a user or a data processing device associated with the user and are accessible over a network such as the internet or a cellular network.

The term 'machine-readable' means in a format that is processable by a data processing device. Processing includes but is not limited to one or more of: identifying and displaying one or more data items stored in a machine-readable data structure on a display device; and extracting one or more data items stored in a machine-readable data structure and performing one or more calculations on said data items.

Step (a) of the first aspect of the present disclosure involves establishing a desired patient endpoint. The desired patient endpoint may be a goal that is expected to be achieved by the administration of the co-therapy regimen to the patient. The desired patient endpoint may be set by a healthcare provider, the patient, or a combination thereof. The desired patient outcome may be specific to the particular disease or condition, and/or the patient. It may be a single goal, or a group of goals. The endpoint may be that which forms the optimal balance between beneficial effects of the therapy and side effects, as determined by the clinician, the patient, or ideally both.

The desired patient endpoint should be represented and stored in a manner such that it accessible to, and readable by, a data processing device so that it may be used in processing step (d). The desired patient endpoint can be stored either by the patient or by a healthcare provider. It will be understood that storing can thus include entering the desired patient endpoint into a data processing device using a user interface thereof, where the data processing device creates a machine-readable representation of the desired patient endpoint and stores this representation in a non-volatile storage medium or media. The non-volatile storage medium or media are preferably Cloud-based, and accessible via a network such as the internet or a cellular network.

The machine-readable representation of the desired patient endpoint may be stored in a structured format such as an element in a database or a semi-structured format such as an element node in an XML document. The representation of the desired patient endpoint may comprise one or more data types, including but not limited to one or more strings, integers, double precision values, floating point values, Boolean values, and combinations thereof. A suitable representation for a desired patient endpoint will be determined by a skilled person given the particular circumstances of any specific scenario.

Preferably, the machine-readable representation of the desired patient endpoint is stored securely, to protect patient confidentiality. It is preferably necessary to supply one or more authorisation credentials to gain access to the stored representation of the desired patient endpoint. The representation of the desired patient endpoint may additionally or alternatively be stored in an encrypted format. Such techniques are known per se and accordingly are not described in detail here.

The desired patient endpoint may comprise the successful treatment of a disease or condition so that the patient no longer suffers from said disease or condition or a symptom thereof. It may include amelioration of a side-effect of a disease or condition, a side-effect attributed to a pharmaceutical drug, such as one administered to the patient to treat a disease or condition, and/or amelioration of the side-effects of a non-pharmacological therapy. In this case, the patient may have input in defining the desired patient endpoint in relation to the tolerable side-effects or the like. The desired patient endpoint may be the patient achieving a specific value on a known symptom scale, such as a pain value as defined by the Wong-Baker Faces Pain Scale.

The desired patient endpoint may be heavily dependent upon the disease or condition to be treated. If insomnia is the disease or condition, then the desired patient endpoint may comprise the patient having at least about 4 hours sleep, for instance at least about 5 hours sleep, preferably at least about 6 hours sleep, more preferably at least about 7 hours sleep in a 24 hour period, and preferably at night. It may comprise the patient not waking before a certain time in the morning, such as not before about 7 am, for instance not before about 6 am, preferably not before about 5 am, and/or not experiencing difficulty falling asleep. The desired patient endpoint may be that the patient feels that he or she has been getting enough quality sleep over the course of a 5 day period.

If diabetes is the disease or condition, then the desired patient endpoint may comprise the patient having a blood glucose level below a certain amount, such as from about 4.0 to about 7.0 mmol/L pre-prandial, preferably from about 4.0 to about 5.9 mmol/L pre-prandial. The desired patient endpoint may comprise the treatment or amelioration of a side-effect of having diabetes, such as fatigue or burning sensations in feet. It may comprise reducing the side-effects due to medicine used to treat diabetes, such as metformin related gut side effects.

If hypertension is the disease or condition, then the desired patient endpoint may comprise the patient having a blood pressure at rest of from about 110 to about 130 mmHg systolic, and optionally having from about 60 to about 85 mmHg diastolic. It may comprise a reduction in symptoms associated with hypertension, such as reduction in headaches. Conversely, it may be desired to minimise the frequency of symptoms related to postural hypotension, such as light headedness, in those patients who have periods during the day of lower blood pressure, recognising that blood pressure often varies in any one individual during the day and from day to day. The reduction in said symptoms may be the reduction to a certain frequency of incidence.

If opiate dependency is the disease or condition, then the desired patient endpoint may comprise the patient discontinuing use of opiates. It may comprise the reduction in tolerance to opioids and/or reducing or ameliorating withdrawal symptoms, for instance nausea, diarrhoea, trouble sleeping/insomnia, jitteriness, sweating, pain recrudescence or low mood.

It is envisaged that the desired patient endpoint may change as treatment of the disease or condition progresses. For instance, the patient and/or healthcare provider may decide that that endpoint may not be attainable, or that there is no need to reach said endpoint. For instance, the desired patient endpoint for insomnia may be that the patient has 7 hours sleep in a 24 hour period, however, a patient may feel that 6 hours sleep in a 24 hour period is adequate. In this case, the desired patient endpoint may be changed accordingly. Similarly, if the desired endpoint is that the patient has 6 hours sleep in a 24 hour period, and the patient feels that 7 hours sleep in a 24 hour period is achievable, then the desired patent endpoint may be changed accordingly.

Step (b) of the first aspect of the present disclosure involves identifying the patient position relative to the desired patient endpoint. The patient position should be related to desired patient endpoint. For instance, if the desired patient endpoint is the patient having a blood pressure at rest of from about 110 to about 130 mmHg systolic, then the patient position may be the patient's current resting blood pressure. If the desired patient endpoint is the patient having a blood glucose level of between about 4.0 to about 5.9 mmol/L pre-prandial, then the patient position may be the patient's current blood glucose level pre-prandial.

The difference between the patient position and the desired patient endpoint may be used to define the scope of treatment expected to be delivered by the co-therapy regimen. For example, if the desired patient endpoint is the patient having a blood pressure at rest of from about 110 to about 130 mmHg systolic, and the patient's current resting blood pressure is about 170 mmHg systolic, then the aim of the treatment would to reduce the patient's resting blood pressure by about 40 mmHg to about 50 mmHg. In the circumstance that the patient's average blood pressure was 125 mmHg, but at times during a day it could be 115 mmHg or 145 mmHg, and when 115 mmHg this was associated with troublesome dizziness, but if a mean blood pressure of 135 mmHg is the target, no periods of symptomatic low blood pressure occur, then a target of 135 mmHg may be preferred by both patient and clinician.

In a further variation, the initial target may be so adjusted to a systolic of 135 mmHg, but with the passage of further time, for example 3 months, the patient's vasculature may adapt such they are now able to tolerate a systolic of 115 mmHg and therefore the new average systolic target is 125 mmHg.

The patient position relative to the desired patient endpoint should be stored in the same manner as described above in respect of the desired patient endpoint so that it may be used in processing step (d). Preferably, the machine-readable representation of the patient position is stored in the same format as the machine-readable representation of the desired patient endpoint, as this may enable or assist with calculation of the difference between the patient position and the desired patient endpoint by a data processing device.

Step (c) of the first aspect of the present disclosure involves generating or modifying a dataset relating to the patient, based on one or more patient-related measurements.

As used herein, a "dataset" is a machine-readable collection of information, or data, that is composed of separate elements, which elements can be manipulated either individually or collectively by a processor, such as a processor in a data processing device. The information, or data, in the dataset is related to the patient. A dataset can take many forms including a structured, semi-structured or unstructured dataset.

Without being bound by theory, it is understood that patient-related measurements are those that are expected to be useful in generating a co-therapy regimen suitable for use in the treatment of the disease or condition to which the method relates. The dataset may therefore help to predict the patient's susceptibility to treatment of a particular disease with the co-therapy.

A combination of the patient's susceptibility to treatment and the scope of treatment, defined by the patient position relative to the desired patient endpoint, may be use to provide the co-therapy regime.

It is envisaged that the claimed method may be used to help predict the efficacy and/or suitability of a co-therapy regime for a particular patient.

If a dataset relating to the patient is not available, perhaps because the patient has just enrolled onto the system, then said dataset is generated. This involves creating a dataset containing the relevant data as discussed below, and linking the dataset to the patient, such as by using a patient code or some other unique identifier. If a suitable dataset relating to the patient is already available to the data processing device, then the dataset may be modified by appending one or more relevant data entries to the dataset and/or replacing one or more relevant data entries already present in the dataset, said data being that as discussed below.

The patient-related measurement may include
a) one or more physiological measurements;
b) one or more patient-centred outcomes;
c) one or more environmental measurements, such as temperature, humidity, and/or light intensity, local to the patient; and/or
d) one or more behavioural factor measurements.

The term "patient-related measurement" refers to data that is related to the patient. A patient-related measurement may be data relating directly to the patient, such as a "physiological measurement", e.g. resting heart rate, systolic blood pressure at rest, blood glucose level, and biomarker concentration in blood. Such measurements may be taken by a patient, a healthcare provider or by a device, such as an electronic device, such as a smartphone or other handheld device. In any case, the one or more patient-related measurements used in the method of the present disclosure may be dependent upon the specific disease or condition to be treated.

A patient-related measurement may be a patient-centred outcome.

A "patient-centred outcome" is an assessment of the patient's beliefs, opinions and needs, optionally in conjunction with a healthcare provider's expertise, in relation to their treatment. A patient-centred outcome may comprise an indication of whether the patient is receiving suitable relief from one or more symptoms of the disease or condition from which they are being treated. For instance, it could be an indication of whether the treatment is providing enough pain relief, or enough sleep, to the patient. It may also comprise negative effects of the treatment including various side effects and the preferred trade-off between beneficial effects and side effects of the treatment.

A patient-centred outcome may be reported and/or recorded by the patient, a healthcare provider, or an electronic device, such as a smartphone or other handheld device. If the patient-centred outcome is reported and/or recorded by the patient it may be referred to as a patient-reported outcome.

A patient-centred outcome, and therefore a patient-reported outcome, may be qualitative or quantitative. A patient-centred outcome, and especially a patient-reported outcome, may need to be mapped onto a predefined scale to create a mapped patient-centred outcome. This is preferable if the patient-centred outcome (or patient-reported outcome) is qualitative. It may be preferable that a patient-reported outcome is provided via a questionnaire. Further, the particular predefined scale may be personalised for the patient.

A patient-related measurement may relate to the patient's environment, such as the patient's local environment. In this case, an environmental measurement may be made. Suitable environmental measurements may include temperature, humidity, and/or light intensity, such as daily light exposure, daily average temperature, maximum/minimum daily temperature, and daily rainfall. The environmental measurement may be reported and/or recorded by the patient, a healthcare provider, or an electronic device, such as a smartphone or other handheld device.

A patient-related measurement may be a behavioural factor measurement. These are measurements of specific behaviours of the patient, such as total number of steps taken per day, minutes of cardiovascular training performed per day, and units of alcohol consumed per week. A behavioural factor measurement may be qualitative or quantitative. A behavioural factor measurement may need to be mapped onto a predefined scale to create a mapped behavioural factor measurement. This is preferable if the behavioural factor measurement is qualitative.

As mentioned, patient-related measurements useful in the method of the present disclosure may be dependent upon the disease or condition that it intended to be treated. Again, the patient-related measurements that may be expected to be useful in generating a co-therapy regimen suitable for use in the treatment of the disease or condition will be known.

The data may be inputted directly into the dataset in raw form, or may be processed prior to being input into the dataset. Such processing may involve taking the data and modifying or evaluating one or more of the data's constituent data points prior to inputting it into the dataset. For example, the patient may provide information in the form of a patient-centred outcome, such as the level of pain he or she is experiencing by pointing to a face on the Wong-Baker Faces Pain Scale, which is then converted into a numeric value according to that scale, with the numeric value being input into the dataset.

Patient-related measurements may be taken by the patient, and/or by a healthcare provider. For instance, the patient may take their own blood pressure, heart rate, or blood glucose level. Alternatively, a healthcare provider may take the patient's blood pressure, heart rate, or blood glucose level. A patient-related measurement may require input from multiple people. For example, the patient may provide a blood sample at a specific time, which is then analysed for a certain biomarker concentration, said concentration then inputted into the dataset. The measurements may be actively obtained, for instance when the patient and/or healthcare provider make an action specifically to obtain a measurement, such as providing a blood sample at a specific time. The measurements may be obtained passively, such as via a wearable technology, preferably linked to an electronic device, such as a smartphone or other handheld device.

Patient-related measurements may be obtained from other sources, such as online databases or third-parties. For example, data may be taken from online weather websites to estimate the daily light exposure for the patient based upon the patient's location.

It will be apparent that while each of the patient-related measurements used in the method of the present disclosure should be expected to influence the co-therapy regimen, the level of influence may be dependent upon the specific patient-related measurement, the patient and/or the disease or condition to which the method relates. It is therefore envisaged that the step of generating or modifying the dataset relating to the patient may include the step of applying a weighting factor to each of the one or more patient-related measurements.

Step (d) of the first aspect of the present disclosure involves processing the dataset, the patient position and the desired patient endpoint, to generate the co-therapy regimen. The processing may be carried out using a processor, such as a processor in a data processing device.

Without being bound by theory, the difference between the patient position and the desired patient endpoint may define the scope of treatment to be delivered to the patient, and the dataset may be used to predict the susceptibility of the patient to the treatment. The dataset, the patient position and the desired patient endpoint may therefore be processed to provide a patient-specific dosage regimen (personalised medicine) that is expected to treat the particular disease or condition.

In the processing step, the dataset, the patient position and the desired patient endpoint may be processed using a rules-based system to produce the regimen for the co-therapy. Alternatively, the dataset, the patient position and the desired patient endpoint may be processed using one or more machine learning algorithms to produce the regimen for the co-therapy. As a further alternative, a hybrid approach is also contemplated in which both a rules-based system and one or more machine learning algorithms are used to process the dataset, patient position and desired patient endpoint.

The term "rules-based system" means a system that operates according to a set of one or more predefined rules. The one or more rules may be encoded in a computer-interpretable format such as one or more modules of program code. The one or more rules may be encoded to take advantage of known or hypothesised relationships between a patient position and their desired patient endpoint, and/or observations in changes in the behaviour, health or other such parameters of the patient as the treatment progresses, in order to produce a recommended regimen for the co-therapy. Other factors not relating to the condition of the patient, such as regulatory constraints, may be additionally or alternatively encoded into the one or more rules.

One or more of the rules may be modified or deleted to take account of new observations, hypotheses and/or knowledge as and when appropriate. One or more new rules may be added to an existing set of one or more rules, with the one or more new rules perhaps being introduced to take account of new observations, hypotheses and/or knowledge, and/or changes in a regulatory framework.

A rule may reference another entity such as the above-discussed dataset. A rule may specify that a particular action is or is not taken based on a property of the entity; e.g. a value of a data point in the dataset. A rule may involve instructing a data processing device to perform a calculation, which calculation perhaps involves or is based upon a property of the entity, where an action being performed as an outcome of the rule depends on an output of the calculation. A rule may reference one or more external sources of data, such as a database of a medical institution, with the action specified by the rule being dependent on data retrieved from said database.

The term "machine learning algorithm" takes its usual meaning in the art and includes any algorithm that employs any currently known or later developed machine learning technique or techniques. Examples of machine learning algorithms include but are not limited to a neural network, a support vector machine, a Naïve Bayes Classifier, a K-Means Clustering Algorithm, and the like. Deep learning techniques may be used. The machine learning algorithm may employ supervised, semi-supervised and/or unsupervised learning techniques.

In the context of the present disclosure, the at least one machine learning algorithm is used either alongside or in place of the above-discussed rules-based system and has the objective of producing the regimen for the co-therapy. The one or more machine learning algorithms may use one or more data points from the above-discussed dataset for inputting into a model, where the output of the model is a regimen for the co-therapy. The model may be trained using one or more data points from the above-discussed dataset. Training of a machine learning model, and use of a trained model, are known per se in the art and thus are not discussed in detail here.

The co-therapy may comprise pharmacological therapies, non-pharmacological therapies or a mixture thereof. Specifically, the co-therapy used in the methods of the present disclosure may comprise (i) two or more pharmacological therapies;
(ii) one or more pharmacological therapies and one or more non-pharmacological therapies, preferably wherein the one or more non-pharmacological therapy is cognitive behavioural therapy; or (iii) two non-pharmacological therapies, preferably wherein at least one non-pharmacological therapy is cognitive behavioural therapy.

In a second aspect of the present disclosure, there is provided a method of treating a patient suffering from a disease or condition, the method comprising the steps of
a) selecting a co-therapy suitable to treat the disease or condition;
b) establishing a desired patient endpoint;
c) identifying the patient position relative to the desired patient endpoint;
d) generating or modifying a dataset relating to the patient, based on one or more patient-related measurements;
e) processing the dataset, the patient position and the desired patient endpoint to produce a regimen for the co-therapy; and
f) administering the co-therapy to the patient according to the regimen.

As it will be appreciated, steps (b) to (e) of the second aspect of the present disclosure correspond to steps (a) to (d) of the first aspect of the present disclosure, the definition of which for the first aspect of the present disclosure applies equally to the second aspect of the present disclosure.

In addition to the above, step (a) of the second aspect of the present disclosure involves selecting a co-therapy suitable to treat the disease or condition. The range of co-therapies that may be suitable for use in the treatment of a specific disease or condition are known, particularly to healthcare providers.

Step (f) of the second aspect of the present disclosure involves administering the co-therapy to the patient according to the regimen. As mentioned above, it is within the scope of the present disclosure that the co-therapy is administered to the patient according to the regimen in any suitable way.

It is envisaged that successful treatment of the disease or condition may require a plurality (i.e. more than one) of treatment cycles. A treatment cycle can comprise each of steps (a) to (f) of the second aspect of the present disclosure. Therefore, the method of treatment according to the second aspect of the present disclosure may include carrying out steps (a) to (f) and then repeating steps (a) to (f) at least one time, such as one, two, three, four, five, six, seven, eight, nine, ten times.

In the method of treatment according to the second aspect of the present disclosure, it is preferable not to change the co-therapy between treatment cycles. Therefore, it is preferable that the method comprises a plurality of treatment cycles, wherein the treatment cycle comprises steps (b) to (f).

When a plurality of treatment cycles is to be used, the frequency of the cycles may be dependent upon the specific therapies being administered to the patient. In particular, the time period between processing step (e) of the second aspect of the present disclosure (i.e. the step of processing the dataset, the patient position and the desired patient endpoint to produce a regimen for the co-therapy) of two consecutive cycles may be dependent upon the timeframe within which one would expect the patient to respond to the therapies. For example, if the patient is expected to have a fast response time to a treatment, such as the use of insulin to treat diabetes, processing step (e) may be carried out at least about 1 hour, such as at least about 2 hours, for instance at least about 3 hours, for examples at least about 4 hours, after processing step (e) was last performed. If the patient is expected to have an intermediate response time to a treatment, such as the use of melatonin to treat insomnia, processing step (e) may be carried out at least about 1 day, such as at least about 2 days, for instance at least about 3 days, for examples at least about 4 days, after processing step (e) was last performed. If the patient is expected to have a slow response time to a treatment, such as the use of cognitive behavioural therapy in the treatment of opioid dependence, processing step (e) may be carried out at least about 1 week, such as at least about 2 weeks, for instance at least about 3 weeks, for examples at least about 4 weeks, after processing step (e) was last performed.

Notwithstanding the above, a benefit of the present disclosure is that a patient's co-therapy regimen may be altered within a shorter time period than that set by two consecutive visits to a healthcare provider (the first visit providing the patient with a co-therapy regimen and the second visit altering the co-therapy regimen based upon the patient's response to the co-therapy regimen). The frequency of visits to a healthcare provider may be dependent upon the type of therapies being administered to the patient, therefore, it is preferable that the time period between processing step (e) of the second aspect of the present disclosure of two consecutive cycles is less than the frequency of such visits. For instance, processing step (e) may be carried out less than about 10 weeks, such as less than about 8 weeks, for instance less than about 6 weeks, for examples less than about 5 weeks, after processing step (e) was last performed. In certain cases, processing step (e) may be carried out less than about 4 weeks, such as less than about 2 weeks, for instance less than about 1 week, for examples less than about 4 days, i.e. less than about 2 days, after processing step (e) was last performed.

In an exemplary embodiment, in step (d) the dataset may be modified based on one or more patient-related measurements. However, step (e) is not performed until an elapsed time has passed, wherein the elapsed time is equal to a length of time between the production of a regimen for the co-therapy according to step (e) and the most recent modification to the dataset in step (d). Essentially, step (d) may be carried out a plurality of times until a certain time has elapsed since the production of a regimen for the co-therapy in step (e) has occurred, after which step (e) is performed. The elapsed time may be the time noted above between processing step (e) of two consecutive cycles.

When a plurality of treatment cycles is used, the method may comprise after step (e) an additional step of adjusting the regimen for the co-therapy based upon the difference between the regimen provided in step (e) and the regimen provided in step (e) of the previous cycle. In this case, the adjusted regimen for the co-therapy may be adjusted by 60, 70, 80, or 90% of that difference. For instance, when an 80% threshold is adopted, in the case when the regimen provided in the previous cycle comprises 100 mg of a drug, and the new regimen comprises 200 mg of the drug, the method may return a regimen of 180 mg to be administered to the patient in step (f). This additional step may help dampen the method's reaction to a change in the patient dataset and prevent the patient's regimen for the co-therapy oscillating between a dose of the drug that is too high and a dose that is too low to attain the desired patient endpoint.

The processing step may also limit the maximum and minimum amount that one or more drugs may be administered to the patient, and/or the amount by which the regimen for the co-therapy is changed, based upon regulatory matters, patient or healthcare provider instruction, or other factors.

Further, it may not be necessary to once again establish the desired patient endpoint so the method of the second aspect of the present disclosure may comprise a plurality of treatment cycles, wherein the treatment cycle comprises steps (c) to (f).

Also envisaged in the present disclosure is a co-therapy for use in the treatment of a patient suffering from a disease or condition, the co-therapy provided by a method comprising the steps of the first aspect of the present disclosure and all embodiments thereof.

The co-therapy of generated or provided by the methods of the present disclosure may be used to treat or prevent any disease or condition. This includes both acute and chronic diseases or conditions, such as those selected from the group consisting of pre-diabetes, diabetes; cardiovascular disease; neurodegeneration diseases, such as Mild Cognitive Impairment (MCI), Alzheimer's disease and Parkinson's disease; atrial fibrillation; attention deficit hyperactivity disorder (ADHD); autoimmune diseases, such as ulcerative colitis, lupus erythematosus, Crohn's disease, coeliac disease, Hashimoto's thyroiditis, bipolar disorder; cerebral palsy such as dyskinetic and athetoid; chronic graft-versus-host disease; hepatitis; chronic kidney disease; arthritis and chronic osteoarticular diseases, such as osteoarthritis and rheumatoid arthritis; cancer; obesity; asthma; sinusitis; cystic fibrosis; tuberculosis; chronic obstructive airways disease, bronchitis; bronchiolitis; pulmonary fibrosis; pain, including chronic pain syndromes; depression; eating disorders; polycystic ovary syndrome; epilepsy; fibromyalgia; viral diseases, such as HIV/AIDS; Huntington's disease; hypotension; hypertension; allergic rhinitis; multiple sclerosis; fatigue states, including chronic fatigue syndrome; insomnia; narcolepsy; osteoporosis; periodontal disease; postural orthostatic tachycardia syndrome; sickle cell anemia and other hemoglobin disorders; sleep apnea; thyroid disease; reflux, including gastroesophageal reflux; vomiting; irritable bowel syndrome (IBS); inflammatory bowel disease (IBD); peptic ulcer; acute urticarial; atopic dermatitis; contact dermatitis; seborrheic dermatitis; headache, including migraine, cluster headache, and tension-type headache; addiction, such as drug addiction, in particular opiate dependency, cocaine, alcohol, or nicotine addiction and chronic usage thereof; thromboembolic disease; hair loss; hormone replacement therapy; psychiatric disorders, such as psychosis, anxiety and depression; endocrine dysfunctions, including growth hormone deficiency, hypothyroidism; haematological disorders, including clotting factor deficiencies or low levels of white or red blood cells; neurodevelopmental delay (NDD) disorders, including Autistic Spectrum Disorder (ASD), Smith Magenis Syndrome and ADHD; parasomnias, including REM and NREM parasomnias and nightmare disorders; sleep movement disorders, such as restless legs syndrome and periodic limb movement disorder, circadian rhythm disorders (including such disorders brought on by shift work and/or jet lag); chorea and tic disorders.

Diseases and conditions in which the present disclosure is particular useful are insomnia, obesity, diabetes, in particular type-II diabetes, hypertension, and opiate dependency.

Data collected when the disease or condition is insomnia may relate to one or more of the possible data for insomnia in the table below.

| Possible data for insomnia |
|---|
| Melatonin (current dosage regimen) |
| Melatonin metabolite levels in urine at various time points |
| Daily light exposure |
| CBT usage |
| Sleep quality |

| -continued |
|---|
| Possible data for insomnia |
| Tiredness level |
| Perceived impairment of ability |
| Caffeine intake |
| Pain |
| Anxiety |
| Stress |
| Insomnia duration (from start of suffering) |
| Basal heart rate |
| Metabolic rate |
| Nocturnal cognitive arousal, such as determined by non-invasive brain wave (EEG) recordings |
| Multiple sleep latency test results |
| Underlying medical conditions/patient history |
| Oxygen haemoglobin desaturation during REM sleep |
| Other medication |
| Gender |
| Age |
| Ethnicity |
| Smoking history |
| Alcohol use |
| Illicit substance use |
| Nocturnal Polysomnogram |
| Actigraphy |
| Daytime Sleepiness |
| Depression |
| Oximetry |
| Chronotype |
| Maintenance of Wakefulness Test |
| Arousal Index |
| Any other sleep disorder (e.g. presence of restless legs syndrome) |
| Nocturnal panic |
| Pain |
| Night sweats |

Data collected when the disease or condition is type-II diabetes may relate to one or more of the possible data for type-II diabetes in the table below.

| Possible data for type-II diabetes |
|---|
| Metformin usage (current and historic dosage regimen) |
| GLP-1 agonist usage (current and historic dosage regimen) |
| Insulin usage (current and historic dosage regimen) |
| Other diabetes medication usage (current and historic dosage regimen) |
| Fasting blood glucose level |
| Current blood glucose level |
| Diet |
| CBT usage |
| Sleep quality |
| Activity levels |
| Fatigue levels |
| Energy levels |
| Weight |
| Mood |
| Basal heart rate |
| Metabolic rate |
| Underlying medical conditions/patient history |
| Other medication |
| Gender |
| Age |
| Ethnicity |
| Smoking history |
| Alcohol use |
| Bowel function (inc. degree of bloating and cramping, bowel openings, looseness of stool, nausea degree) |
| Timing of symptoms |
| Gut microbiome analysis |

As mentioned above, the co-therapies suitable to treat diseases and conditions are well known. However, when the disease or condition is insomnia, it may be advantageous for the co-therapy to consist of two therapies, the first therapy comprising melatonin and the second therapy comprising cognitive behavioural therapy for insomnia (CBTi).

When the disease or condition is diabetes, particular type-II diabetes, it may be advantageous for the co-therapy to consist of two therapies, the first therapy comprising metformin and the second therapy comprising cognitive behavioural therapy.

When the disease or condition is diabetes, particular type-II diabetes, it may be advantageous for the co-therapy to consist of two therapies, the first therapy comprising metformin and the second therapy comprising a GLP-1 agonist.

When the disease or condition is diabetes, particular type-II diabetes, it may be advantageous for the co-therapy to consist of two therapies, the first therapy comprising a GLP-1 agonist and the second therapy comprising cognitive behavioural therapy.

When the disease or condition is diabetes, particular type-II diabetes, it may be advantageous for the co-therapy to consist of three therapies, the first therapy comprising metformin, the second therapy comprising cognitive behavioural therapy and the third comprising a GLP-1 agonist.

When the disease or condition is hypertension it may be advantageous for the co-therapy to consist of two therapies, the first therapy comprising amlodipine and the second therapy comprising cognitive behavioural therapy.

When the disease or condition is opiate dependency it may be advantageous for the co-therapy to consist of two or three therapies. When the co-therapy consists of two therapies, it is preferable that the first therapy comprises morphine, and the second therapy comprises an $\alpha_2$ agonist or cognitive behavioural therapy. When the co-therapy consists of three therapies, it is preferable that the first therapy comprises morphine, the second therapy comprises an $\alpha_2$ agonist, and the third co-therapy comprises cognitive behavioural therapy. In each case, it is preferable that the $\alpha_2$ agonist is clonidine.

A system 100 suitable for carrying out any of the above-described methods is shown in FIG. 1. System 100 includes a data processing device 105 that is communicatively coupled to a database 110 that stores a dataset as discussed earlier in this specification. Database 110 is stored on a storage medium, e.g. a Cloud-based storage medium.

Data processing device 105 comprises at least one processor and is configured to carry out any of the methods described in this specification, or one or more steps thereof. Data processing device 105 may operate in accordance with one or more rules, optionally stored in database 110, and/or data processing device 105 may be configured to execute one or more machine learning tasks. The machine learning tasks include any combination of: training a model using data from a dataset stored in database 110 and/or using a trained model to classify an input such as data from a dataset stored in database 110.

Data processing device 105 can be configured to perform tasks including: receiving data from a patient device 115; generating a dataset for storage in database 110; appending data to an existing dataset stored in database 110; transmitting information and/or commands to patient device 115 and/or clinician data processing device 130, and the like. Data processing device 105 may be a server that hosts a website or portal which is accessible to one or both of patient device 115 and clinician data processing device 130.

In the illustrated embodiment, patient device 115 is a smartphone, optionally comprising a sensor 120. However, the present disclosure is not limited in this respect and patient device 115 can take many other forms, including but not limited to a mobile telephone, a tablet computer, a desktop computer, a voice-activated computing system, a laptop, a gaming system, a vehicular computing system, a wearable device, a smart watch, a smart television, an internet of things device, a medicament-dispensing device and a device including a drug pump.

Patient device 115 is communicatively coupled to data processing device 105 via a network 125. In the illustrated embodiment network 125 is the internet, but the present disclosure is not limited in this respect and network 125 could be any network that enables communication between patient device 115 and data processing device 105, such as a cellular network or a combination of the internet and a cellular network.

Patient device 115 is configured to gather data relating to a patient and/or the immediate environment of the patient and to transmit at least some of said gathered data to data processing device 105. Patient device 115 may gather data using sensor 120, which can be any combination of: a light sensor such as a camera, a temperature sensor, an acoustic sensor such as a microphone, an accelerometer, an air pressure sensor, an airborne particulate sensor, a global positioning sensor, a humidity sensor, an electric field sensor, a magnetic field sensor, a moisture sensor, an air quality sensor and a Geiger counter, and/or any other such sensor capable of determining a characteristic of the patient and/or the patient's immediate environment.

Alternatively, sensor 120 can be omitted from patient device 115. In that case, information about the patient and/or the immediate environment of the patient can be obtained via other mechanisms including manual data entry using a human interface device of patient device 115.

It will be appreciated that system 100 may include more than one patient device that is similar to patient device 115. It is contemplated that a single patient may use more than one patient device to collect data and feed it into system 100.

Patient device 115 may have one or more applications installed on a storage medium associated with the patient device (not shown), the one or more applications configured to control data acquisition via sensor 120 and/or to assist the patient in providing data relating to their current condition and/or their immediate environment.

System 100 optionally includes a clinician data processing device 130 that is communicatively coupled via network 125 to data processing device 105. The clinician data processing device 130 is broadly similar to patient device 115, offering a similar set of functionality. Specifically, the clinician data processing device 130 enables data relating to the patient and/or the immediate environment of the patient to be collated and transmitted to data processing device 105. Clinician data processing device 130 is contemplated as being physically located at a clinician's premises during its use, such as a doctor's surgery, a pharmacy or any other healthcare institution, e.g. a hospital. Clinician data processing device 130 may include one or more sensors like sensor 120, and/or be configured to control one or more separate sensors like sensor 120, which sensors are capable of gathering information about the patient and/or their local environment.

It is also contemplated that clinician data processing device 130 is typically used by a medically trained person with appropriate data security clearance, such that more advanced functionality may be available than via the patient device 115. For example, the clinician data processing device 130 may be able to access a medical history of the patient, generate a prescription for the patient, place an order for medication, etc. Access to functionality may be controlled by a security policy implemented by data processing device 105.

It is contemplated that system 100 could omit patient device 115 altogether, in which case all reporting of data to data processing device 105 is handled by clinician data processing device 130. This configuration may find particularly utility in situations where a patient is incapable of providing data to data processing device via a patient device, e.g. due to their current medical condition or non-compliance.

Figure 2:
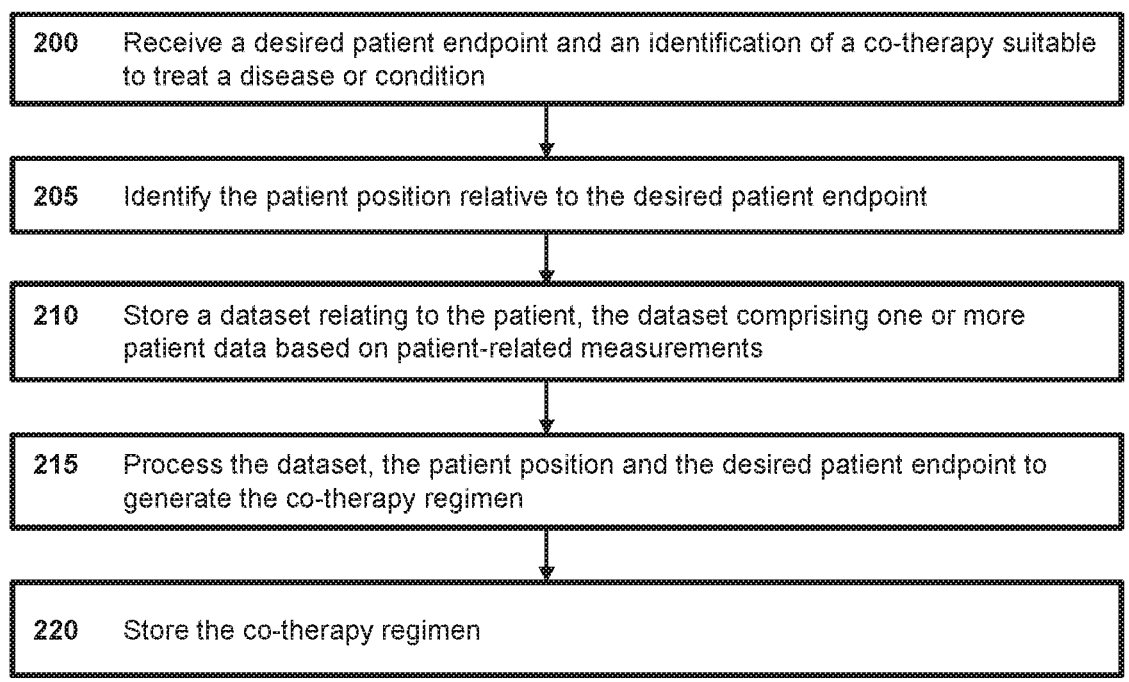
FIG. 2 shows a method that can be performed by one or more components of the system of FIG. 1 in accordance with an embodiment.

FIG. 2 shows a method that can be performed by data processing device 105 in accordance with an embodiment.

In step 200, data processing device 105 receives a desired patient endpoint. The desired patient endpoint may be received from patient device 115 or clinician data processing device 130. Data processing device 105 may store the desired patient endpoint in database 110 in a machine-processable format. The desired patient endpoint may be provided by a clinician via a user interface of clinician data processing device 130, or it may be provided by a patient via a user interface of patient device 115.

Data processing device 105 also receives in step 200 an identification of a co-therapy suitable to treat a disease or condition that the patient corresponding to the desired patient endpoint is suffering from. Data processing device 105 may store the identification in database 110 in a machine-processable format. The identification may be provided by a clinician via a user interface of clinician data processing device 130, or it may be retrieved from database 110 or another data source (e.g. a healthcare institution's database) based upon an identification of the disease or condition that the patient is suffering from, or based upon a patient unique identifier.

In step 205, data processing device 105 identifies the patient position relative to the desired patient endpoint. Data processing device 105 may receive patient-related information from one or both of the patient device 115 and the clinician data processing device 130 in order to identify the patient position.

The patient-related information includes but is not limited to: information entered by the patient using a user interface of patient device 115; data gathered by sensor 120 of patient device 115, if present; information entered by a clinician or other healthcare professional using a user interface of clinician data processing device 130; and/or data gathered by a sensor of clinician data processing device, if present.

In the case where sensor data is provided, data processing device 105 preferably identifies the patient position by processing the patient-related information using one or more rules stored in database 110 and/or using a trained machine learning model stored in database 110.

In step 210, data processing device 105 stores a dataset relating to the patient, the dataset comprising one or more patient data based on patient-related measurements. The patient-related measurements include but are not limited to: measurements entered by the patient using a user interface of patient device 115; measurements performed by sensor 120 of patient device 115, if present; measurements entered by a clinician or other healthcare professional using a user interface of clinician data processing device 130; and/or measurements performed by a sensor of clinician data processing device, if present.

In the case where a dataset relating to the patient is already present in database 110, data processing device preferably appends the patient data to this existing dataset as part of the storing operation. If no dataset relating to the patient is found in database 110, storing preferably includes creating a blank dataset, assigning a unique patient identifier to the blank dataset and populating the blank dataset with the patient data. The unique patient identifier is associated with the patient and can be generated according to any known unique identifier generation scheme.

Data processing device 105 may be configured to apply a weighting factor to each of the patient-related measurements received in step 210 when generating the patient data. The weighting factor expresses a relative importance of a particular patient-related measurement relative to other patient-related measurements. Data processing device 105 may generate an individual weighting factor for each of the patient-related measurements. A given weighting factor may have the same value or a different value to another weighting factor.

The weighting factors may be defined by a clinician in conjunction with the patient. Preferably, data processing device 105 first receives a range for each weighting factor, and subsequently receives a value for each weighting factor that is within the respective range. The selection within the range can be based upon patient preferences, such as the desire for a particular benefit and/or the level of desire to avoid a particular side effect, for example.

Preferably, each weighting factor is selected so as to minimise the time it is expected for the patient to move from the patient position to the desired patient endpoint. A probabilistic prediction of a patient condition, e.g. a Bayesian prediction, can be used to predict the future condition of the patient using current and historical patient measurements as a function of each weighting factor. The set of weighting factors is selected based on the prediction. The set of weighting factors that minimises the time it is expected for the patient to move from the patient position (i.e. their current state) to the desired patient endpoint is preferably selected. One or more weighting factors can be adjusted as necessary during the course of a treatment should the actual progress of the patient deviate significantly from the predicted progress of the patient.

In step 215, data processing device 105 processes the dataset, the patient position and the desired patient endpoint to generate a co-therapy regimen. This step can comprise processing the dataset, patient position and desired patient endpoint using one or more rules, and/or using one or more machine learning algorithms. Regardless of the technique used to generate a co-therapy regimen, the result of step 215 is a co-therapy regimen that is predicted, suggested or otherwise thought to be likely to be effective in moving the patient closer towards the desired patient endpoint.

In cases where the co-therapy includes a component requiring the patient to administer one or more drugs that are provided in a fixed dosage form, e.g. pills containing a set amount of active ingredient, step 215 preferably includes a comparison of the dosage requirements of the generated co-therapy regimen against the dosages of the relevant drug(s) that are available to the patient.

In the case where the patient cannot administer the relevant drug(s) in the amount required by the generated co-therapy regimen, data processing device 105 may adjust the generated co-therapy regimen to require an amount of the relevant drug(s) that minimises the difference between the amount required by the initially generated regimen and the possible combinations of dosages administrable by the patient.

For example, consider the case where a patient is required to administer drug X as part of a co-therapy. The patient has access to pills containing drug X, where each pill contains 10 mg of drug X. Data processing device 105 initially generates a co-therapy regimen that calls for 32 mg of drug X. The patient cannot administer precisely 32 mg, so data processing device 105 adjusts the co-therapy regimen to require 30 mg of drug X, this being administrable by the patient ingesting three 10 mg pills.

In another example, data processing device 105 initially generates a co-therapy regimen that calls for 38 mg of drug X. The patient cannot administer precisely 38 mg, so data processing device 105 adjusts the co-therapy regimen to require 40 mg of drug X, this being administrable by the patient ingesting four 10 mg pills.

Data processing device 105 can alternatively be configured to adjust the generated co-therapy regimen to require an amount of the relevant drug(s) that is equal to the closest value administrable by the patient that does not exceed the dosage initially generated by data processing device 105.

Under this alternative implementation, using the example of drug X above, in the case that the data processing device initially generates a co-therapy regimen that calls for 38 mg of drug X, the co-therapy regimen may be adjusted to require 30 mg of drug X, this being administrable by the patient ingesting three 10 mg pills. This alternative implementation may be preferred in situations where it is considered undesirable to exceed a dosage recommendation.

Information relating to the dosage forms available to the patient may be provided to data processing device 105 by patient device 115 and/or clinician data processing device 130. This information may be stored in the dataset relating to the patient as part of step 210.

As part of step 215, data processing device 105 can additionally or alternatively be configured to check whether a change in a dosage amount of one or more constituents of the co-therapy is greater than a threshold level. The threshold change can be expressed as a percentage change of the dosage amount of the most recently generated co-therapy regimen, i.e. the regimen currently being followed by the patient. The threshold level is preferably set based on a prediction as to the greatest change in dosage that a patient can safely tolerate. The threshold level may be received by data processing device 105 from a clinician, perhaps via clinician data processing device 130.

In the case that the change in dosage amount is greater than the threshold level, data processing device 105 is configured to adjust the co-therapy regimen such that the dosage amount is equal to the threshold level. This adjustment can be performed in addition to the adjustment based on dosage amounts available to the patient, or in the alternative. This adjustment has the effect of ensuring that the patient does not follow a co-therapy regimen that proscribes a change in dosage amount that is thought to be too large for the patient to tolerate.

In the case that the change in dosage amount is less than or equal to the threshold level, data processing device 105 is configured to make no adjustment to the co-therapy regimen.

In step 220, data processing device 105 stores the co-therapy regimen that was generated in step 215. The co-therapy regimen may be stored in database 110, preferably in association with the patient and more preferably in the dataset relating to the patient. Metadata such as the date and time at which the co-therapy regimen was generated may also be stored in association with the co-therapy regimen.

In the case where any adjustment to the generated co-therapy regimen of the type discussed above has been performed in step 215, an indication that this adjustment was performed may also be stored by data processing device 105 as part of step 220, e.g. within metadata associated with the co-therapy regimen. A notification may additionally or alternatively be transmitted to patient device 115 and/or clinician data processing device 130 by data processing device 105, to inform one or both parties that an adjustment to the co-therapy regimen has been made.

The timing of said transmission may be optimised based on the regiment and the most recent patient data (for example the patient's location or state of mind).

Step 220 may also comprise transmitting the co-therapy regimen to one or both of patient device 115 and clinician data processing device 130, perhaps for display on a display of one or both of these devices. Additional actions that data processing device 105 may perform as part of step 220 include any combination of: generating a prescription for the patient based on the co-therapy regimen; instructing the patient to follow the co-therapy regimen; and controlling a drug administration device to cause at least one drug associated with the co-therapy regimen to be administered to the patient. Data processing device 105 may effect these additional actions by transmitting control commands to other devices, including but not limited to patient device 115 and/or clinician data processing device 130.

Preferably, data processing device 105 is configured to make a determination as to whether the co-therapy regimen generated in step 215 is compliant with requirements, guidelines, etc. of a relevant regulatory framework. Checking for regulatory compliance may include checking that a recommended dosage of a drug that is part of the co-therapy is within a dosage range that has regulatory approval, for example. If the recommended dosage is non-compliant, remedial action by the data processing device may be taken, such as: setting a dosage of the drug to a value that has regulatory approval and which is closest to the recommended value; and/or transmitting a message to clinician data processing device 130 requesting further instructions.

Database 110 may store a regulatory data table that identifies, on a drug by drug basis, dosage ranges having regulatory approval, for use by data processing device 105 when checking that the co-therapy regimen generated in step 215 is regulatory compliant.

It will be appreciated that steps 200 to 220 can be performed by data processing device 105 a plurality of times for a single patient. In this way, a dynamic co-therapy is provided that is adaptive to the changing condition of the patient as the treatment progresses. Without being bound by theory, it is thought that the adaptation of a co-therapy as treatment progresses may result in a more effective treatment for the patient. For example, the patient may achieve, or get close to achieving, the desired patient endpoint, perhaps in a relatively rapid manner.

It will also be appreciated that in some cases it is appropriate to keep the desired patient endpoint and co-therapy constant over the course of a treatment. In such cases, for the second and subsequent iteration of the process of FIG. 2, data processing device 105 can omit step 200 as the desired patient endpoint and identification of a suitable co-therapy are unchanged.

It is contemplated that, when performing one or more steps of FIG. 2, data processing device 105 may receive one or more pieces of information in a human-intelligible format that is not suitable, or at least not optimised, for storage in the dataset stored in database 110. For example, the patient-related measurements may include patient-reported outcomes provided in the form of natural language or as values within a constrained response framework. In such cases, data processing device 105 is preferably configured to map the patient-reported outcomes onto a predefined scale to create mapped patient-reported outcomes. In this way the 'messy' information received by data processing device 105 can be converted into 'clean' data before being stored in database 110.

It is also contemplated that a variant of step 200 may be performed in the second and subsequent iteration of the process of FIG. 2, in which only the desired patient endpoint is received by data processing device 105. This variant is particularly suited for use in a case where the co-therapy remains constant but the desired patient endpoint may vary over time.

Figure 3:
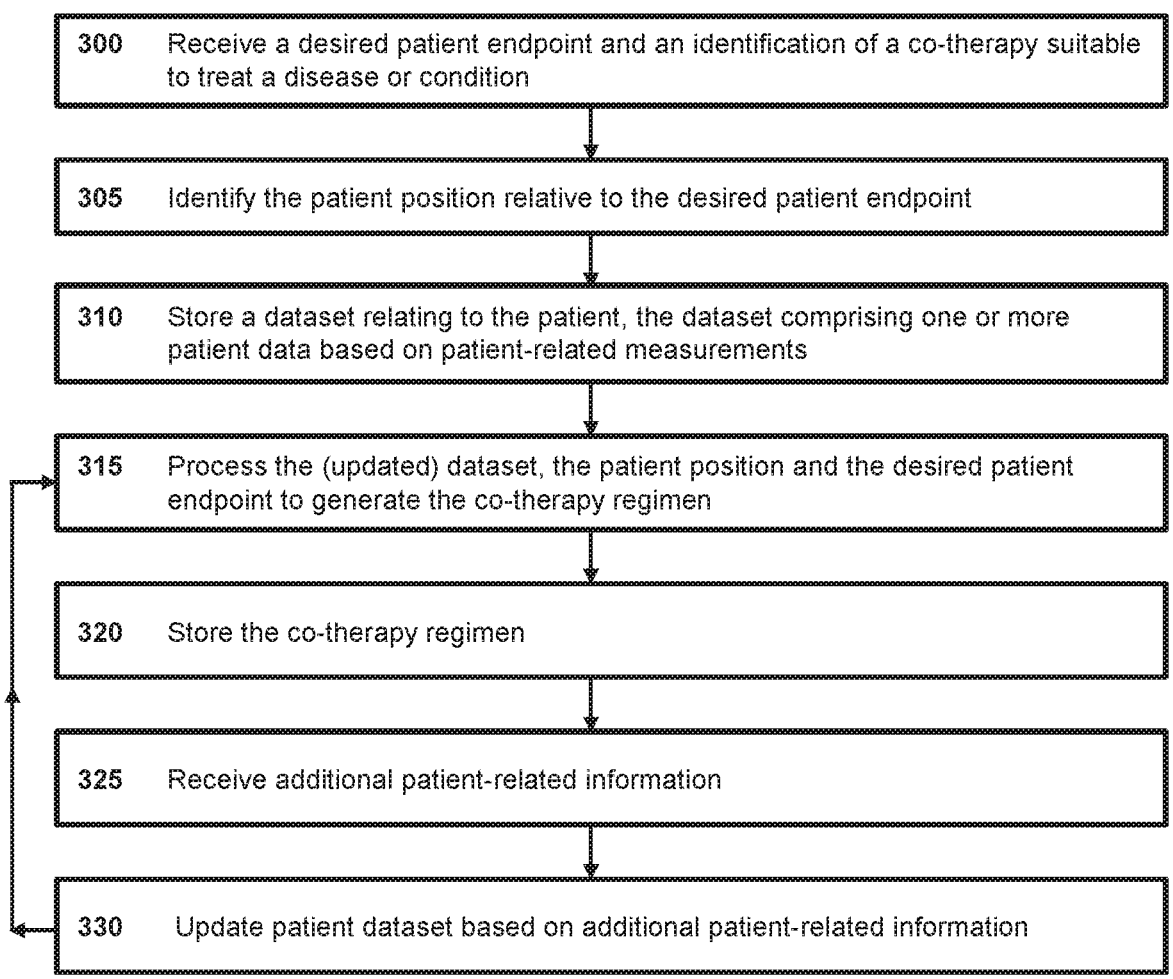
FIG. 3 shows a method that can be performed by one or more components of the system of FIG. 1 in accordance with another embodiment.

An exemplary embodiment in which data processing device 105 performs more than one iteration is shown in FIG. 3. Steps 300 to 320 are the same as steps 200 to 220, respectively, so are not described in detail again here. The following sets out additional considerations that are preferably present in an iterative process like that of FIG. 3.

In step 325, data processing device 105 receives additional patient-related information.

The patient-related information can be of the type discussed earlier in this specification and is received subsequent to the patient-related information received in connection with step 205.

In step 330, data processing device 105 updates the dataset relating to the patient discussed above in connection with step 210. Updating may include appending patient data based on the additional patient-related information received in step 325 to the dataset relating to the patient, or overwriting some or all of the existing content of the dataset relating to the patient with patient data that is based on the additional patient-related information received in step 325.

At this point, the process loops back to step 315. In this case the data processing device 105 processes the dataset, the patient position and the desired patient endpoint to generate the co-therapy regimen in the manner described earlier in connection with step 215.

The co-therapy regimen generated by this second iteration of step 315 can be the same or different to the co-therapy regimen generated by the first iteration of step 315. Any differences are attributable to data processing device 105 making use of a revised patient dataset that includes or is based on the additional patient-related information received in step 325.

Data processing device 105 makes use of the revised patient dataset to provide a recommended co-therapy regimen when performing the second iteration of step 315 that is responsive to the actual state of the patient. It will thus be appreciated that steps 315 to 330 can be repeated many times in the manner shown in FIG. 3 to enable a dynamic co-therapy regimen to be devised, which dynamic regimen is responsive to the actual state of the patient.

It will be appreciated that data processing device 105 may at any point receive a new desired patient endpoint, e.g. from patient device 115 or clinician data processing device 130. Responsive to receiving a new desired patient endpoint, data processing device 105 is configured to replace the existing desired patient endpoint with the new desired patient endpoint. Thus, at the next iteration of the process of FIG. 3, a co-therapy regimen is generated based on the new desired patient endpoint.

Figure 4:
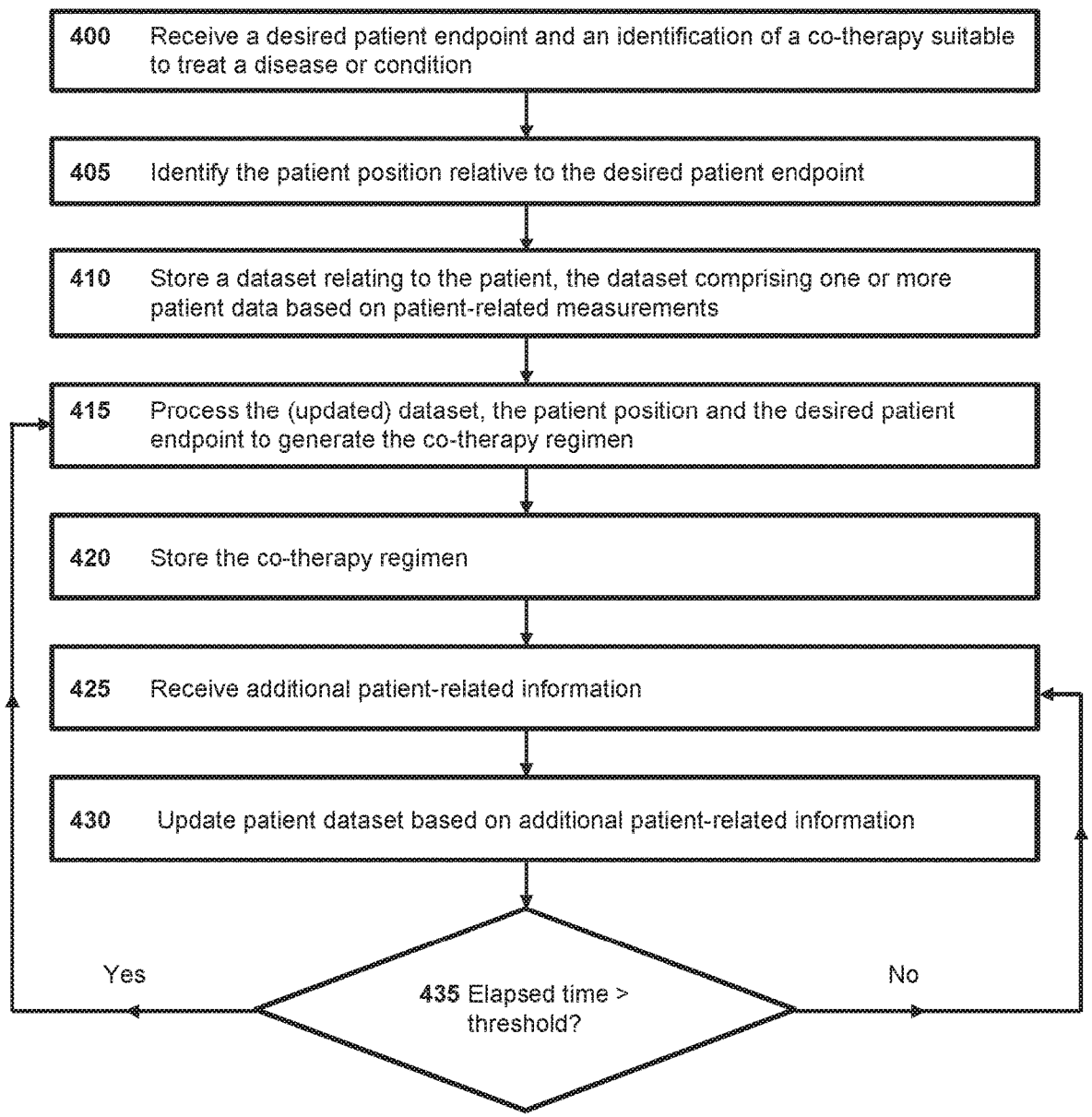
FIG. 4 shows a method that can be performed by one or more components of the system of FIG. 1 in accordance with a further embodiment.

Another exemplary embodiment in which data processing device 105 performs more than one iteration is shown in FIG. 4. Steps 400 to 430 are the same as steps 300 to 330, respectively, so are not described in detail again here. The following sets out additional considerations that are preferably present in an iterative process like that of FIG. 4.

In step 435, data processing device 105 calculates whether an elapsed time associated with the additional patient-related information exceeds a threshold value. The elapsed time is equal to a length of time between the most recent update to the co-therapy regimen 415 and the most recent update to the patient dataset 420. A time at which a patient-related measurement was made can be established by generating a timestamp at the time the measurement was made, which timestamp can be appended to, or otherwise associated with, the measurement.

As an example, in the case where a processing device 105 generates an updated co-therapy regimen at 9 am and measures their blood sugar level at 12 pm on the same day, the elapsed time associated with the measurement is 3 hours.

The threshold value is set according to the considerations discussed earlier in this specification relating to the timeframe within which one would expect the patient to respond to the therapies, e.g. the time noted above between processing step (e) of two consecutive cycles in relation to the second aspect of the present disclosure. As set out above, preferably the threshold value is set such that it is greater than or equal to the duration of a timeframe within which one would expect the patient to respond to the therapies and less than a time between two consecutive patient visits to a healthcare provider.

The threshold value may be fixed at the outset of a course of treatment and remain static throughout, or the threshold value may be varied as a course of treatment is ongoing, i.e. from iteration to iteration of the process of FIG. 4. Variations may be based on analysis of the timeframe over which a particular patient responds to a particular co-therapy, which analysis may be performed by data processing device 105 on the patient dataset established in step 310.

In the case that the elapsed time is calculated to be less than the threshold, the process returns to step 425 in which data processing device 105 awaits further patient-related information. Without being bound by theory, it is believed that it may be counterproductive in at least some cases to adjust the co-therapy regimen over a timeframe that is significantly shorter than an expected timeframe for the patient to respond to the therapies. An 'overshoot/undershoot' scenario where the regimen oscillates for some time before reaching a stable level may thus be avoided, or at least the time spent oscillating may be reduced.

In the case that the elapsed time is calculated to be greater than the threshold, the process loops back to step 415 and proceeds as described in respect of FIG. 3. It is preferred in such a case that any patient-related information gathered during one or more iterations in which the elapsed time was calculated to be less than the threshold time is used in the generation of the co-therapy regimen of step 415. In this manner, patient-related information that is gathered too rapidly for immediate processing is still made use of.

As in the case of the process of FIG. 3, it will be appreciated that data processing device 105 may at any point receive a new desired patient endpoint, e.g. from patient device 115 or clinician data processing device 130. Responsive to receiving a new desired patient endpoint, data processing device 105 is configured to replace the existing desired patient endpoint with the new desired patient endpoint. Thus, at the next iteration of the process of FIG. 4 for which the elapsed time is greater than the threshold, a co-therapy regimen is generated based on the new desired patient endpoint.

It will be appreciated that any of the methods described herein, or parts thereof, can be encoded by computer-readable instructions and stored on a non-transitory computer-readable medium. Any part of the systems and methods described above can thus be implemented by a computer executing appropriate instructions stored on a non-transitory computer-readable medium. A computer readable medium storing such instruction is thus also within the scope of the present disclosure.

The foregoing discussion discloses embodiments in accordance with the present disclosure. As will be understood, the approaches, methods, techniques, materials, devices, and so forth disclosed herein may be embodied in additional embodiments as understood by those of skill in the art, it is the intention of this application to encompass and include such variation. Accordingly, this disclosure is illustrative and should not be taken as limiting the scope of the following claims.

The following are numbered embodiments exemplifying specific embodiments of the present disclosure.

Embodiment 1

A method of generating a co-therapy regimen for a patient suffering from a disease or condition, the method comprising the steps of:
  a) establishing a desired patient endpoint;
  b) identifying the patient position relative to the desired patient endpoint;
  c) generating or modifying a dataset relating to the patient, based on one or more patient-related measurements; and
  d) processing the dataset, the patient position and the desired patient endpoint to generate the co-therapy regimen.

Embodiment 2

A method of treating a patient suffering from a disease or condition, the method comprising the steps of:
  a) selecting a co-therapy suitable to treat the disease or condition;
  b) establishing a desired patient endpoint;
  c) identifying the patient position relative to the desired patient endpoint;
  d) generating or modifying a dataset relating to the patient, based on one or more patient-related measurements;
  e) processing the dataset, the patient position and the desired patient endpoint to produce a regimen for the co-therapy; and
  f) administering the co-therapy to the patient according to the regimen.

Embodiment 3

The method of embodiment 2, wherein the method comprises a plurality of treatment cycles, wherein the treatment cycle comprises steps (c) to (f), such as steps (b) to (f).

Embodiment 4

The method of any preceding embodiment, wherein, in the processing step, the dataset, the patient position and the desired patient endpoint are processed using a rules-based system to produce the regimen for the co-therapy.

Embodiment 5

The method of any one of embodiments 1 to 3, wherein, in the processing step, the dataset, the patient position and the desired patient endpoint are processed using a machine learning algorithm to produce the regimen for the co-therapy.

Embodiment 6

The method of any preceding embodiment, wherein the co-therapy comprises
  (i) two or more pharmacological therapies;
  (ii) one or more pharmacological therapies and one or more non-pharmacological therapies, preferably wherein the one or more non-pharmacological therapy is cognitive behavioural therapy; or
  (iii) two non-pharmacological therapies, preferably wherein at least one non-pharmacological therapy is cognitive behavioural therapy.

Embodiment 7

The method of any preceding embodiment, wherein the disease or condition is selected from the group consisting of pre-diabetes; diabetes; cardiovascular disease; neurodegeneration diseases, such as Mild Cognitive Impairment (MCI), Alzheimer's disease and Parkinson's disease; atrial fibrillation; attention deficit hyperactivity disorder (ADHD); autoimmune diseases, such as ulcerative colitis, lupus erythematosus, Crohn's disease, coeliac disease, Hashimoto's thyroiditis, bipolar disorder; cerebral palsy such as dyskinetic and athetoid; chronic graft-versus-host disease; hepatitis; chronic kidney disease; arthritis and chronic osteoarticular diseases, such as osteoarthritis and rheumatoid arthritis; cancer; obesity; asthma; sinusitis; cystic fibrosis; tuberculosis; chronic obstructive airways disease, bronchitis; bronchiolitis; pulmonary fibrosis; pain, including chronic pain syndromes; depression; eating disorders; polycystic ovary syndrome; epilepsy; fibromyalgia; viral diseases, such as HIV/AIDS; Huntington's disease; hypotension; hypertension; allergic rhinitis; multiple sclerosis; fatigue states, including chronic fatigue syndrome; insomnia; narcolepsy; obesity; osteoporosis; periodontal disease; postural orthostatic tachycardia syndrome; sickle cell anaemia and other haemoglobin disorders; sleep apnoea; thyroid disease; reflux, including gastroesophageal reflux; vomiting; irritable bowel syndrome (IBS); inflammatory bowel disease (IBD); peptic ulcer; acute urticarial; atopic dermatitis; contact dermatitis; seborrheic dermatitis; headache, including migraine, cluster headache, and tension-type headache; addiction, such as drug addiction, in particular opiate dependency, cocaine, alcohol, or nicotine addiction and chronic usage thereof; thromboembolic disease; hair loss; hormone replacement therapy; psychiatric disorders, such as psychosis, anxiety and depression; endocrine dysfunctions, including growth hormone deficiency, hypothyroidism; haematological disorders, including clotting factor deficiencies or low levels of white or red blood cells; neurodevelopmental delay (NDD) disorders, including Autistic Spectrum Disorder (ASD), Smith Magenis Syndrome and ADHD; parasomnias, including REM and NREM parasomnias and nightmare disorders; sleep movement disorders, such as restless legs syndrome and periodic limb movement disorder, circadian rhythm disorders (including such disorders brought on by shift work and/or jet lag); chorea and tic disorders.

Embodiment 8

The method of any preceding embodiment, wherein
a) the disease or condition is insomnia and the co-therapy comprises melatonin and cognitive behavioural therapy for insomnia (CBTi);
b) the disease or condition is diabetes and the co-therapy comprises metformin and cognitive behavioural therapy;
c) the disease or condition is diabetes or obesity and the co-therapy comprises a GLP1-agonist and cognitive behavioural therapy;
d) the disease or condition is diabetes or obesity and the co-therapy comprises a GLP1-agonist and metformin;
e) the disease or condition is diabetes or obesity and the co-therapy comprises a GLP1-agonist, metformin and cognitive behavioural therapy;
f) the disease or condition is hypertension and the co-therapy comprises amlodipine and cognitive behavioural therapy; or
g) the disease or condition is opiate dependency and the co-therapy comprises
  (i) morphine and an $\alpha_2$ agonist;
  (ii) morphine and cognitive behavioural therapy; or
  (iii) morphine, an $\alpha_2$ agonist and cognitive behavioural therapy, preferably wherein the $\alpha_2$ agonist is clonidine.

Embodiment 9

The method of any preceding embodiment, wherein the desired patient endpoint is amelioration of the disease or condition, amelioration of the symptoms associated with the disease or condition, amelioration of the side-effects of a pharmacological therapy, and/or amelioration of the side-effects of a non-pharmacological therapy.

Embodiment 10

The method of any preceding embodiment, wherein the one or more patient-related measurements includes
a) one or more physiological measurements;
b) one or more patient-centred outcomes;
c) one or more environmental measurements, such as temperature, humidity, and/or light intensity, local to the patient; and/or
d) one or more behavioural factor measurements.

Embodiment 11

The method of embodiment 10, wherein the one or more patient-centred outcomes includes one or more patient-reported outcomes, preferably provided via a questionnaire.

Embodiment 12

The method of embodiment 11, further comprising: mapping the one or more patient-reported outcomes onto a predefined scale to create mapped patient-reported outcomes, wherein the step of generating or modifying a dataset, based on one or more patient-related measurements comprises generating or modifying the dataset based on the mapped patient-reported outcomes.

Embodiment 13

The method of any preceding claim, wherein the step of generating or modifying a dataset relating to the patient, based on one or more patient-related measurements, comprises applying a weighting factor to each of the one or more patient-related measurements.

Embodiment 14

A system for generating a co-therapy regimen for a patient suffering from a disease or condition, the system comprising at least one data processing device having at least one processor, wherein the system is configured to:
  a) receive an identification of a co-therapy suitable to treat the disease or condition;
  b) receive a desired patient endpoint and a patient position, wherein the patient position is defined relative to the desired patient endpoint;
  c) store a dataset relating to the patient, the dataset comprising one or more patient data based on patient-related measurements;
  d) process the dataset, the patient position and the desired patient endpoint to generate a regimen for the co-therapy; and
  e) store the regimen in a database.

Embodiment 15

The system of embodiment 14, wherein the at least one data processing device is further configured to, after step e):
  f) receive additional patient-related information;
  g) update the dataset relating to the patient based on the additional patient-related information;
  h) process the updated dataset, the patient position and the desired patient endpoint to generate an updated regimen for the co-therapy; and
  i) store the updated regimen in the database.

Embodiment 16

The system of embodiment 14, where the at least one data processing device is further configured to, after step e);
  f) receive additional patient-related information;
  g) calculate whether an elapsed time associated with the additional patient-related information exceeds a threshold value;
  in the affirmative:
  h) update the dataset relating to the patient based on the additional patient-related information;
  i) process the updated dataset, the patient position and the desired patient endpoint to generate an updated regimen for the co-therapy; and
  j) store the updated regimen in the database;
  in the negative:
  k) update the dataset relating to the patient based on the additional patient-related information.

Embodiment 17

The system of any one of embodiment 14 to 16, wherein the system is further configured to:
  receive sensor data gathered by at least one sensor; and
  determine at least one of the one or more patient data based at least in part on the received sensor data.

Embodiment 18

The system of embodiment 17, wherein the at least one sensor is an environmental sensor and/or a physiological sensor.

Embodiment 19

The system of embodiment 18, wherein the environmental sensor is any combination of a light sensor, a temperature sensor, an acoustic sensor, an accelerometer, an air pressure sensor, an airborne particulate sensor, a global positioning sensor, a humidity sensor, an electric field sensor, a magnetic field sensor, a moisture sensor, an air quality sensor, a sensor capable of detecting proximity to a WiFi transmitter and/or a cellular network base station, and a Geiger counter.

Embodiment 20

The system of embodiment 18 or embodiment 19, wherein the physiological sensor is any biological or endpoint based biomarker sensor.

Embodiment 21

The system of any one of embodiments 14 to 20, wherein the system further comprises a human interface device, and wherein the system is configured to output the regimen using the human interface device.

Embodiment 22

The system of any one of embodiments 14 to 21, wherein the system is configured to process the dataset, the patient position and the desired patient endpoint using a rule-based system to generate the regimen for the co-therapy.

Embodiment 23

The system of any one of embodiments 14 to 22, wherein the system is configured to process the dataset, the patient position and the desired patient endpoint using a machine learning algorithm to generate the regimen for the co-therapy.

Embodiment 24

The system of any one of embodiments 14 to 23, wherein the co-therapy comprises
(i) two or more pharmacological therapies;
(ii) one or more pharmacological therapy and one or more non-pharmacological therapy, preferably wherein the one or more non-pharmacological therapy is cognitive behavioural therapy; or
(iii) two non-pharmacological therapies, preferably wherein at least one non-pharmacological therapy is cognitive behavioural therapy.

Embodiment 25

The system of any one of embodiments 14 to 24, pre-diabetes; diabetes; cardiovascular disease; neurodegeneration diseases, such as Mild Cognitive Impairment (MCI), Alzheimer's disease and Parkinson's disease; atrial fibrillation; attention deficit hyperactivity disorder (ADHD); autoimmune diseases, such as ulcerative colitis, lupus erythematosus, Crohn's disease, coeliac disease, Hashimoto's thyroiditis, bipolar disorder; cerebral palsy such as dyskinetic and athetoid; chronic graft-versus-host disease; hepatitis; chronic kidney disease; arthritis and chronic osteoarticular diseases, such as osteoarthritis and rheumatoid arthritis; cancer; obesity; asthma; sinusitis; cystic fibrosis; tuberculosis; chronic obstructive airways disease, bronchitis; bronchiolitis; pulmonary fibrosis; pain, including chronic pain syndromes; depression; eating disorders; polycystic ovary syndrome; epilepsy; fibromyalgia; viral diseases, such as HIV/AIDS; Huntington's disease; hypotension; hypertension; allergic rhinitis; multiple sclerosis; fatigue states, including chronic fatigue syndrome; insomnia; narcolepsy; osteoporosis; periodontal disease; postural orthostatic tachycardia syndrome; sickle cell anaemia and other haemoglobin disorders; sleep apnoea; thyroid disease; reflux, including gastroesophageal reflux; vomiting; irritable bowel syndrome (IBS); inflammatory bowel disease (IBD); peptic ulcer; acute urticarial; atopic dermatitis; contact dermatitis; seborrheic dermatitis; headache, including migraine, cluster headache, and tension-type headache; addiction, such as drug addiction, in particular opiate dependency, cocaine, alcohol, or nicotine addiction and chronic usage thereof; thromboembolic disease; hair loss; hormone replacement therapy; psychiatric disorders, such as psychosis, anxiety and depression; endocrine dysfunctions, including growth hormone deficiency, hypothyroidism; haematological disorders, including clotting factor deficiencies or low levels of white or red blood cells; neurodevelopmental delay (NDD) disorders, including Autistic Spectrum Disorder (ASD), Smith Magenis Syndrome and ADHD; parasomnias, including REM and NREM parasomnias and nightmare disorders; sleep movement disorders, such as restless legs syndrome and periodic limb movement disorder, circadian rhythm disorders (including such disorders brought on by shift work and/or jet lag); chorea and tic disorders.

Embodiment 26

The system of any one of embodiments 14 to 25, wherein
a) the disease or condition is insomnia and the co-therapy comprises melatonin and cognitive behavioural therapy for insomnia (CBTi);
b) the disease or condition is diabetes and the co-therapy comprises metformin and cognitive behavioural therapy;
c) the disease or condition is diabetes or obesity and the co-therapy comprises a GLP1-agonist and cognitive behavioural therapy;
d) the disease or condition is diabetes or obesity and the co-therapy comprises a GLP1-agonist and metformin;
e) the disease or condition is diabetes or obesity and the co-therapy comprises a GLP1-agonist, metformin and cognitive behavioural therapy;
f) the disease or condition is hypertension and the co-therapy comprises amlodipine and cognitive behavioural therapy; or
g) the disease or condition is opiate dependency and the co-therapy comprises
   (i) morphine and an $\alpha_2$ agonist;
   (ii) morphine and cognitive behavioural therapy; or
   (iii) morphine, an $\alpha_2$ agonist and cognitive behavioural therapy, preferably wherein the $\alpha_2$ agonist is clonidine.

Embodiment 27

The system of any one of embodiments 14 to 26, wherein the desired patient endpoint is amelioration of the disease or condition, amelioration of the symptoms associated with the disease or condition, amelioration of the side-effects of a pharmacological therapy, and/or amelioration of the side-effects of a non-pharmacological therapy.

Embodiment 28

The system of any one of embodiments 14 to 27, wherein the one or more patient-related measurements includes
a) one or more physiological measurements;
b) one or more patient-centred outcomes;
c) one or more environmental measurements, such as temperature, humidity, and/or light intensity, local to the patient; and/or
d) one or more behavioural factor measurements.

Embodiment 29

The system of embodiment 28, wherein the one or more patient-centred outcomes includes one or more patient-reported outcomes, preferably provided via a questionnaire.

Embodiment 30

The system of embodiment 29, wherein the system is further configured to map the one or more patient-reported outcomes onto a predefined scale to create mapped patient-reported outcomes,
wherein the one or more patient data stored in the dataset are based at least in part on the mapped patient-reported outcomes.

Embodiment 31

The system of any one of embodiments 14 to 30, wherein the system is configured to apply a weighting factor to each of the patient-related measurements in order to generate the patient data.

What is claimed is:

1. A method of treating a patient suffering from a disease or condition, the method comprising the steps of:
a) selecting a co-therapy suitable to treat the disease or condition;
b) establishing a desired patient endpoint;
c) identifying the patient position relative to the desired patient endpoint;
d) generating or modifying a dataset relating to the patient, based on one or more patient-related measurements;
e) processing the dataset, the patient position and the desired patient endpoint to produce a regimen for the co-therapy;
f) receiving additional patient-related information;
g) calculating whether an elapsed time associated with the additional patient-related information exceeds a threshold value relating to a timeframe for the patient to respond to the co-therapy, wherein the timeframe is dependent upon the co-therapy being administered;
in the affirmative:
h) updating the dataset relating to the patient based on the additional patient-related information;
i) processing the updated dataset, the patient position and the desired patient endpoint to generate an updated regimen for the co-therapy; and
in the negative:
j) updating the dataset relating to the patient based on the additional patient-related information and maintaining the regimen for the co-therapy; and
the method further comprising:
k) administering the co-therapy to the patient according to the updated regimen in i) or the regimen in e),
wherein the co-therapy comprises a pharmacological therapy and one or more non-pharmacological therapies, and wherein a patient electronic device administers the one or more non-pharmacological therapies, wherein the disease and co-therapy are selected from the group consisting of:
a) the disease or condition is diabetes and the co-therapy comprises metformin and cognitive behavioural therapy;
b) the disease or condition is diabetes or obesity and the co-therapy comprises a GLP1-agonist and cognitive behavioural therapy; or
c) the disease or condition is diabetes or obesity and the co-therapy comprises a GLP1-agonist, metformin and cognitive behavioural therapy.

2. The method of claim 1, further comprising:
receiving sensor data gathered by at least one sensor; and
determining at least one of the one or more patient-related measurements based at least in part on the received sensor data.

3. The method of claim 2, wherein the at least one sensor is an environmental sensor and/or a physiological sensor.

4. The method of claim 3, wherein the environmental sensor is any combination of a light sensor, a temperature sensor, an acoustic sensor, an accelerometer, an air pressure sensor, an airborne particulate sensor, a global positioning sensor, a humidity sensor, an electric field sensor, a magnetic field sensor, a moisture sensor, an air quality sensor, a sensor capable of detecting proximity to a WiFi transmitter and/or a cellular network base station, and a Geiger counter.

5. The method of claim 3, wherein the physiological sensor is a biological or end-point based biomarker sensor.

6. The method of claim 1, wherein the desired patient endpoint is amelioration of the disease or condition, amelioration of the symptoms associated with the disease or condition, amelioration of the side-effects of a pharmacological therapy, and/or amelioration of the side-effects of a non-pharmacological therapy.

7. The method of claim 1, wherein the one or more patient-related measurements includes:
a) one or more physiological measurements;
b) one or more patient-centred outcomes;
c) one or more environmental measurements; and/or,
d) one or more behavioural factor measurements.

8. The method of claim 7, wherein the one or more patient-centred outcomes includes one or more patient-reported outcomes.

9. The method of claim 8, further comprising mapping the one or more patient-reported outcomes onto a predefined scale to create mapped patient-reported outcomes, and wherein one or more patient data stored in the dataset are based at least in part on the mapped patient-reported outcomes.

10. The method of claim 1, further comprising applying a weighting factor to each of the patient-related measurements in order to generate the patient data.

11. The method of claim 1, wherein the method comprises a plurality of treatment cycles, wherein the treatment cycle comprises steps (c) to (k), wherein the frequency of the treatment cycles corresponds to the co-therapy dependent timeframe.

12. The method of claim 1, wherein, in (e), the dataset, the patient position and the desired patient endpoint are processed using a rule-based system to produce the regimen for the co-therapy.

13. The method of claim 1, wherein, in (e), the dataset, the patient position and the desired patient endpoint are processed using a machine learning algorithm to produce the regimen for the co-therapy.

14. The method of claim 1, wherein the one or more patient-centred outcomes includes one or more patient-reported outcomes.

15. The method of claim 14, further comprising:
mapping the one or more patient-reported outcomes onto a predefined scale to create mapped patient-reported outcomes, and wherein the step of generating or modifying a dataset, based on one or more patient-related measurements comprises generating or modifying the dataset based on the mapped patient-reported outcomes.

16. The method of claim 1, wherein the step of generating or modifying a dataset relating to the patient, based on one or more patient-related measurements, comprises applying a weighting factor to each of the one or more patient-related measurements.

17. The method of claim 1, wherein the co-therapy regimen for a patient suffering from a disease or condition comprises a personalised co-therapy regimen for the patient.

18. The method of claim 1, wherein transmitting the updated regimen to at least one of a patient electronic device or a clinician data processing device comprises transmitting the updated regimen to the patient electronic device for one or more of:
generating a prescription for the patient based on the co-therapy regimen; instructing the patient to follow the co-therapy regimen; or
controlling a drug administration device to cause at least one drug associated with the co-therapy regimen to be administered to the patient.

19. A method of treating a patient suffering from a disease or condition, the method comprising the steps of:
a) selecting a co-therapy suitable to treat the disease or condition;
b) establishing a desired patient endpoint;
c) identifying the patient position relative to the desired patient endpoint;
d) generating or modifying a dataset relating to the patient, based on one or more patient-related measurements;
e) processing the dataset, the patient position and the desired patient endpoint to produce a regimen for the co-therapy;
f) receiving additional patient-related information;
g) calculating whether an elapsed time associated with the additional patient-related information exceeds a threshold value relating to a timeframe for the patient to respond to the co-therapy, wherein the timeframe is dependent upon the co-therapy being administered;
in the affirmative:
h) updating the dataset relating to the patient based on the additional patient-related information;
i) processing the updated dataset, the patient position and the desired patient endpoint to generate an updated regimen for the co-therapy; and,
in the negative:
j) updating the dataset relating to the patient based on the additional patient-related information and maintaining the regimen for the co-therapy;
the method further comprising:
k) administering the co-therapy to the patient according to the updated regimen in i) or the regimen in e),
wherein the co-therapy comprises a pharmacological therapy and one or more non-pharmacological therapies, and wherein a patient electronic device administers the one or more non-pharmacological therapies, wherein the disease and co-therapy are selected from the group consisting of:
the disease or condition is insomnia and the co-therapy comprises melatonin and cognitive behavioural therapy for insomnia (CBTi); or
the disease or condition is opiate dependency and the co-therapy comprises:
(i) morphine and cognitive behavioural therapy; or,
(ii) morphine, an $\alpha_2$ agonist and cognitive behavioural therapy.

20. The method of claim 19, wherein:
the $\alpha_2$ agonist is clonidine.

21. The method of claim 19, wherein the method comprises a plurality of treatment cycles, wherein the treatment cycle comprises steps (c) to (k), wherein the frequency of the treatment cycles corresponds to the co-therapy dependent timeframe.

22. A method of treating a patient suffering from a disease or condition, the method comprising the steps of:
a) selecting a co-therapy suitable to treat the disease or condition;
b) establishing a desired patient endpoint;
c) identifying the patient position relative to the desired patient endpoint;
d) generating or modifying a dataset relating to the patient, based on one or more patient-related measurements;
e) processing the dataset, the patient position and the desired patient endpoint to produce a regimen for the co-therapy;
f) receiving additional patient-related information;
g) calculating whether an elapsed time associated with the additional patient-related information exceeds a threshold value relating to a timeframe for the patient to respond to the co-therapy, wherein the timeframe is dependent upon the co-therapy being administered;
in the affirmative:
h) updating the dataset relating to the patient based on the additional patient-related information;
i) processing the updated dataset, the patient position and the desired patient endpoint to generate an updated regimen for the co-therapy; and,
in the negative:
j) updating the dataset relating to the patient based on the additional patient-related information and maintaining the regimen for the co-therapy;
the method further comprising:
k) administering the co-therapy to the patient according to the updated regimen in i) or the regimen in e),
wherein the co-therapy comprises a pharmacological therapy and one or more non-pharmacological therapies, and wherein a patient electronic device administers the one or more non-pharmacological therapies, wherein the disease or condition is hypertension and the co-therapy comprises amlodipine and cognitive behavioural therapy.

23. The method of claim 22, wherein the method comprises a plurality of treatment cycles, wherein the treatment cycle comprises steps (c) to (k), wherein the frequency of the treatment cycles corresponds to the co-therapy dependent timeframe.

* * * * *